US011111262B2

(12) United States Patent
Bishop et al.

(10) Patent No.: US 11,111,262 B2
(45) Date of Patent: Sep. 7, 2021

(54) C-MANNOSIDE COMPOUNDS USEFUL FOR THE TREATMENT OF URINARY TRACT INFECTIONS

(71) Applicants: GLAXOSMITHKLINE INTELLECTUAL PROPERTY DEVELOPMENT LIMITED, Brentford (GB); FIMBRION THERAPEUTICS, INC., St. Louis, MO (US)

(72) Inventors: Michael Joseph Bishop, Research Triangle Park, NC (US); Eugene L. Stewart, Collegeville, PA (US); Katherine Louisa Widdowson, San Diego, CA (US); James Walter Janetka, St. Louis, MO (US); Laurel Kathryn McGrane, St. Louis, MO (US)

(73) Assignees: GlaxoSmithKline Intellectual Property Development Limited, Brentford (GB); Fimbrion Therapeutics, Inc., St. Louis, MO (US)

( * ) Notice: Subject to any disclaimer, the term of this patent is extended or adjusted under 35 U.S.C. 154(b) by 0 days.

(21) Appl. No.: 17/063,947

(22) Filed: Oct. 6, 2020

(65) Prior Publication Data
US 2021/0017212 A1 Jan. 21, 2021

Related U.S. Application Data

(63) Continuation of application No. PCT/IB2019/055806, filed on Jul. 8, 2019.

(60) Provisional application No. 62/695,993, filed on Jul. 10, 2018, provisional application No. 62/755,588, filed on Nov. 5, 2018.

(51) Int. Cl.
| | |
|---|---|
| *C07H 7/04* | (2006.01) |
| *A61K 9/00* | (2006.01) |
| *A61K 9/20* | (2006.01) |
| *A61K 9/48* | (2006.01) |
| *A61K 45/06* | (2006.01) |

(52) U.S. Cl.
CPC .............. *C07H 7/04* (2013.01); *A61K 9/0014* (2013.01); *A61K 9/0053* (2013.01); *A61K 9/20* (2013.01); *A61K 9/48* (2013.01); *A61K 45/06* (2013.01)

(58) Field of Classification Search
CPC .......... C07H 7/04; A61K 9/0014; A61K 9/20; A61K 9/48
USPC ........................................................ 514/35
See application file for complete search history.

(56) References Cited

U.S. PATENT DOCUMENTS

| | | |
|---|---|---|
| 6,153,396 A | 11/2000 | Hultgren |
| 6,962,791 B2 | 11/2005 | Hultgren |
| 7,790,183 B2 | 9/2010 | Darouiche |
| 8,937,167 B2 | 1/2015 | Janetka |
| 9,567,362 B2 | 2/2017 | Janetka |
| 9,957,289 B2 | 5/2018 | Janetka |
| 10,273,260 B2 | 4/2019 | Janetka |
| 10,738,070 B2 | 8/2020 | Janetka |
| 2007/0167378 A1 | 7/2007 | Saraiva |
| 2008/0171706 A1 | 7/2008 | Berglund |
| 2008/0268006 A1 | 10/2008 | Molin |
| 2010/0015600 A1 | 1/2010 | Barnich |
| 2012/0309701 A1 | 12/2012 | Janetka |
| 2014/0243283 A1 | 8/2014 | Ramtohul et al. |
| 2014/0274930 A1 | 9/2014 | Dietrich |
| 2015/0175644 A1 | 6/2015 | Ernst |
| 2015/0197538 A1 | 7/2015 | Janetka |
| 2016/0145289 A1 | 5/2016 | Janetka |
| 2017/0247401 A1 | 8/2017 | Janetka |
| 2018/0194792 A1 | 7/2018 | Janetka |
| 2019/0106451 A1 | 4/2019 | Janetka |
| 2019/0211045 A1 | 7/2019 | Janetka |
| 2020/0002303 A1 | 1/2020 | Janetka |

FOREIGN PATENT DOCUMENTS

| | | |
|---|---|---|
| EP | 383092 | 1/1990 |
| WO | WO/1995/014028 | 5/1995 |
| WO | WO/2001/100386 | 2/2001 |
| WO | WO/2005/089733 | 9/2005 |
| WO | WO/2011/050323 | 4/2011 |
| WO | WO/2011/073112 | 6/2011 |
| WO | WO/2012/109263 | 8/2012 |
| WO | WO/2012/164074 | 12/2012 |
| WO | WO 2013/134415 | 9/2013 |
| WO | WO 2014/016361 | 1/2014 |
| WO | WO 2014/055474 | 4/2014 |
| WO | WO 2014/100158 | 6/2014 |
| WO | WO 2014/165107 | 10/2014 |
| WO | WO/2014/194270 | 12/2014 |
| WO | WO/2017/021549 | 2/2017 |

(Continued)

OTHER PUBLICATIONS

Abdel-Megeid, F. et al., "Preparation and Some Reactions of O-Glucosyl Derivatives of 2-Thioxo-1,3,4-Oxadiazoles and 2-Thioxo-1,3,4-Thiadiazoles and Their 2-Oxo Analogues", Carbohydrate Res., 59(1):95-102, (1977).

Abgottspon, D. et al., "Development of an Aggregation Assay to Screen FimH Antagonists", J Microb Methods, 82(3):249-55, (2010).

(Continued)

*Primary Examiner* — Shaojia A Jiang
*Assistant Examiner* — Michael C Henry
(74) *Attorney, Agent, or Firm* — Carly A. Shanahan

(57) ABSTRACT

Disclosed herein are new C-mannoside compounds and compositions and their application as pharmaceuticals for the treatment of human disease. Methods of inhibition of FimH activity in a human subject are also provided for the treatment diseases such as urinary tract infection.

4 Claims, No Drawings

(56) References Cited

FOREIGN PATENT DOCUMENTS

| | | |
|---|---|---|
| WO | WO/2017/156508 | 9/2017 |
| WO | WO/2017/165619 | 9/2017 |
| WO | WO/2019/076931 | 4/2019 |

OTHER PUBLICATIONS

Abgottspon, D. et al., "In Vivo Evaluation of FimH Antagonists—A Novel Class of Antimicrobials for the Treatment of Urinary Tract Infection", Chimia, 66(4):166-9, (2012).

Almant M, Moreau V, Kovensky J, et al. "Clustering of *Escherichia coli* type-1 fimbrial adhesins by using multimeric heptyl a-D-mannoside probes with a carbohydrate core," Chem Eur J,17:10029-10038 (2011).

Aronson M, Medalia O, Schori L, et al. "Prevention of colonization of the urinary tract of mice with *Escherichia coli* by blocking of bacterial adherence with methyl alpha-D-mannopyranoside," J Infect Dis, 139:329-332 (1979).

Barras A, Martin FA, Bande O, et al. "Glycan-functionalized diamond nanoparticles as potent *E. coli* anti-adhesives," Nanoscale,5:2307-2316 (2013).

Bognar, R. et al., "N-Glycosyl Derivatives: Part III. The Subsequent Installation of the Aglycone. Synthesis of N- Glycosyl Derivatives of 2-Amino-Thiazole, 2-Amino-1,3,4-Thiadiazole and 5-Amino-1,2,3,4-Thiatriazols", Carbohy Res., 5:320-328, (1967).

Bouckaert, J. et al., "Receptor Binding Studies Disclose a Novel Class of High-Affinity Inhibitors of the *Escherichia coli* FimH Adhesion", Mol Microbial., 55(2):441-55, (2005).

Bouckaert J, Li Z, Xavier C, et al. "Heptyl alpha-D-mannosides grafted on a beta-cyclodextrin core to interfere with *Escherichia coli* adhesion: an in vivo multivalent effect," Chemistry,19:7847-7855 (2013).

Car Z, Hrenar T, Petrović Peroković VP, et al. "Mannosylated N-aryl substituted 3-hydroxypyridine-4-ones: synthesis, hemagglutination inhibitory properties, and molecular modeling," Chem Biol Drug Des,84:393-401 (2014).

Chandrasekaran V, Kolbe K, Beiroth F, et al. "Synthesis and testing of the first azobenzene mannobioside as photoswitchable ligand for the bacterial lectin FimH," Beilstein J Org Chem, 9:223-233 (2013).

Choudhury D, Thompson A, Stojanoff V, et al. "X-ray structure of the FimC-FimH chaperone-adhesin complex from uropathogenic *Escherichia coli*," Science,285:1061-1066 (1999).

Cusumano, C. et al., "Treatment and Prevention of Urinary Tract Infection with Orally Active FimH Inhibitors", Sci Transl Med., 3(109):109ra115, (2011).

de Ruyck J, Lensink MF, Bouckaert J, "Structures of C-mannosylated anti-adhesives bound to the type 1 fimbrial FimH adhesin," IUCrJ,3(Pt 3:163-167 (2016).

Durka, M. et al., "The Functional Valency of Dodecamannosylated Fullerenes with *Escherichia coli* FimH-Towards Novel Oacterial Antiadhesives", Chem Commun., 47(4):1321-3, (2011).

Firon, N. et al., "Aromatic Alpha-Glycosides of Mannose Are Powerful Inhibitors of the Adherence of Type 1 Fimbriated *Escherichia coli* to Yeast and Intestinal Epithelial Cells", Infect Immun., 55(2):472-6, (1987).

Firon, N. et al., "Interaction of Mannose-Containing Oligosaccharides With the Fimbrial Lectin of *Escherichia coli*", Biochem and Biophys Res Commun., 105(4):1426-32, (1982).

Furneaux, R. et al., "New Mannotriosides and Trimannosides as Potential Ligands for Mannose—Specific Binding Oroteins", Can J Chem., 80:964-72, (2002).

Gouin, S. et al., "Synthetic Multimeric Heptyl Mannosides as Potent Antiadhesives of Uropathogenic *Escherichia coli*", Chem Med Chem., 4(5):749-55, (2009).

Grabosch, C. et al., "Squaric Acid Monoamide Mannosides as Ligands for the Bacterial Lectin FimH: Covalent nhibition or Not?", Chem Bio Chem., 12(7):1066-74, (2011).

Guiton, P. et al., "Combinatorial Small-Molecule Therapy Prevents Uropathogenic *Escherichia coli* Catheter-Associated Urinary Tract Infections in Mice", Antimicrob Agents Chemother., 56(9):4738-45, (2012).

Han, Z. et al., "Lead Optimization Studies on FimH Antagonists: Discovery of Potent and Orally Bioavailable Ortho-Substituted Biphenyl Mannosides", J Med Chem., 55(8):3945-59, (2012).

Han, Z. et al., "Structure-Based Drug Design and Optimization of Mannoside Bacterial FimH Antagonists", J Med Chem., 53(12):4779-92, (2010).

Hartmann, M. et al., "The Bacterial Lectin FimH, a Target for Drug Discovery—Carbohydrate Inhibitors of Type 1 Fimbriae-Mediated Bacterial Adhesion", Eur J Org Chem., 2011(20-21):3583-3609 (2011).

Haskins, W. et al., "Relations Between Rotatory Power and Structure in the Sugar Group; Some 2'-Naphthyl L-Thioglycopyranosides and their Acetates", J Am Chem Soc., 69(7):1668-72, (1947).

Hung, C. et al., "Structural Basis of Tropism of *Escherichia coli* to the Bladder During Urinary Tract Infection", Mol Microb., 44(4):903-15, (2002).

Irani, R. et al., "Stannic Chloride Promoted Synthesis of Mannosides", Indian J Chem., Sect. B: Org. Chem. Incl. Med. Chem. 30(5):519-21, (1991), (abstract only).

Jarvis C, Han Z, Kalas V, et al, "Antivirulence isoquinolone mannosides: optimization of the biaryl aglycone for FimH lectin binding affinity and efficacy in the treatment of chronic UTI," ChemMedChem,11(4):367-373 (2016).

Jiang, X. et al., "Antiadhesion Therapy for Urinary Tract Infections—A Balanced PK/PD Profile Proved to Be Key for Success", J Med Chem., 55(10):4700-13, (2012).

Kleeb S, Jiang X, Frei P, et al, "FimH antagonists: phosphate prodrugs improve oral bioavailability," J Med Chem, 59(7):3163-3182 (2016).

Kleeb S, Pang L, Mayer K, et al, "FimH antagonists: bioisosteres to improve the in vitro and in vivo PK/PD profile," J Med Chem, 58(5):2221-2239 (2015).

Klein, T. et al., "FimH Antagonists for the Oral Treatment of Urinary Tract Infections: From Design and Synthesis to in Vitro and in Vivo Evaluation", J Med Chem., 53(24):8627-41, (2010).

Kostakioti, M. et al., "Distinguishing the Contribution of Type 1 Pili from That of other QseB—Misregulated Factors When QseC Is Absent during Urinary Tract Infection", Infect lmmun., 80(8):2826-34, (2012).

Kötter S, Krallmann-Wenzel U, Ehlers S, et al, "Multivalent ligands for the mannose-specific lectin on type 1 fimbriae of *Escherichia coli*: syntheses and testing of trivalent a-D-mannoside clusters," J Chem Soc Perkin Trans I,14:2193-2200 (1998).

Lindhorst, T. et al., "Inhibition of the Type 1 Fimbriae-Mediated Adhesion of *Escherichia coli* to Erythrocytes by Multiantennary [alpha]-mannosyl Clusters: The Effect of Multivalency", Glycoconj J., 15(6):605-13, (1998).

Lindhorst TK, Bruegge K, Fuchs A, et al, "A bivalent glycopeptide to target two putative carbohydrate binding sites on FimH," Beilstein J Org Chem,6:801-809 (2010).

Mydock-McGrane, L. et al., "Antivirulence C-Mannosides as Antibiotic-Sparing, Oral Therapeutics for Urinary Tract Infections", J Med Chem., 59(20):9390-408, (2016).

Nagahori, N. et al., "Inhibition of Adhesion of Type 1 Fimbriated *Escherichia coli* to Highly Mannosylated Ligands", ChemBioChem, 3(9):836-44, (2002).

Neeser J, Koellreutter B, Wuersch P, "Oligomannoside-type glycopeptides inhibiting adhesion of *Escherichia coli* strains mediated by type 1 pili: preparation of potent inhibitors from plant glycoproteins," Infect Immun,52(4):428-436 (1986).

Pang, et al., "FimH Antagonists: Structure-Activity and Structure-Property Relationships for Biphenyl a-D-Mannopyranosides," ChemMedChem 2012, vol. 7, pp. 1404-1422, p. 1408.

Papadopoulos A, Shiao TC, Roy R, "Diazo transfer and click chemistry in the solid phase syntheses of lysine-based glycodendrimers as antagonists against *Escherichia coli* FimH," Mol Pharm,9:394-403 (2012).

(56) References Cited

OTHER PUBLICATIONS

Qian, X. et al., "Arrays of Self-Assembled Monolayers for Studying Inhibition of Bacterial Adhesion", Anal Chem., 74(8):1805-10, (2002).
Rabbani, S. et al., "Expression of the Carbohydrate Recognition Domain of FimH and Development of a Competitive Binding Assay", Anal Biochem., 407(2):188-95, (2010).
Sattigeri, J. et al., "Synthesis and Evaluation of Thiomannosides, Potent and Orally Active FimH Inhibitors", Bioorg Med Chem Lett., 28(17):2993-2997, (2018).
Scharenberg, M. et al., "Target Selectivity of FimH Antagonists", J Med Chem., 55(22):9810-6, (2012).
Scharenberg, M. et al., "A Flow Cytometry-Based Assay for Screening FimH Antagonists", Assay Drug DevTechnol., 9(5):455-65, (2011).
Schierholt A, Hartmann M, Lindhorst TK, "Bi- and trivalent glycopeptide mannopyranosides as inhibitors of type 1 fimbriae-mediated bacterial adhesion: variation of valency, aglycon and scaffolding," Carb Res,346:1519-1526 (2011).
Schönemann W, Kleeb S, Dätwyler P, et al, Prodruggability of carbohydrates—oral FimH antagonists, Can J Chem,94 (11):909-919 (2016).
Schonemann, et al., "Improvement of Agylcone π-Stacking Yields Nanomolar to Sub-nanomolar FimH Antagonists," *ChemMedChem*, 14(7):749-757 (2019).
Schwardt, 0. et al., "Design, Synthesis and Biological Evaluation of Mannosyl Triazoles as FimH Antagonists", Bioorg Med Chem., 19(21):6454-73, (2011).
Shuman, D. et al., "Synthesis and Biological Activity of Certain 8-Mercaptopurine and 6-Mercaptopyrimidine S-Nucleosides", J Med Chem., 12(4):653-7, (1969).
Sperling, O. et al., "Evaluation of the Carbohydrate Recognition Domain of the Bacterial Adhesion FimH: Design, Synthesis and Binding Properties of Mannoside Ligands", Org Biomol Chem., 4(21):3913-3922, (2006).
Stoll, Van A. et al., "The Furocoumarin and the Beta-D-Glucosido-Furocumarinsaure from the Seeds of Coronilla Species", Helvetica Chimica Acta, 33(211-212):1637-47, (1950), (with English abstract).
Taile, V. et al., "Synthesis and Biological Evaluation of Novel 2(4-O-beta-D glucosidoxyphenyl) 4,5-Disubstituted lmidazoles", J Heterocyclic Chem., 47(4):903-7, (2010).
Tomašić T, Rabbani S, Gobec M, et al, "Branched: a-D-mannopyranosides: a new class of potent FimH antagonists," Med Chem Commun,5(8):1247-1253 (2014).
Touaibia, M. et al., "Glycodendrimers as Anti-Adhesion Drugs Against Type 1 Fimbriated *E. coli* Uropathogenic Infections", Mini Rev Med Chem., 7(12):1270-83, (2007).
Touaibia, M. et al., "Mannosylated G(0) Dendrimers with Nanomolar Affinities to *Escherichia coli* FimH", ChemMedChem., 2(8):1190-1201, (2007).
Touaibia, M. et al., "Tri- and Hexavalent Mannoside Clusters as Potential Inhibitors of Type 1 Fimbriated Bacteria Using Pentaerythritol and Triazole Linkages", Chem Commun., (4):380-2, (2007).
Walter, M. et al., "A Modular System for the Preparation of Diazirine-Labeled Mannose Derivatives Using Thiourea Bridging", Synthesis, 6:952-8, (2006).
Wellens, A. et al., "Intervening with Urinary Tract Infections Using Anti-Adhesives Based on the Crystal Structure of the FimH-Oligomannose-3 Complex", PLoS One, 3(4):e2040, (2008).
Wolff, M., "Burger's Medical Chemistry, 5 ed., Part 1", John Wiley & Sons, pp. 975-977, (1995).
Written Opinion and International Search Report issued in PCT/IB2019/055806, dated Oct. 16, 2019.
International Preliminary Report on Patentability issued in PCT/IB2019/055806, dated Jun. 5, 2020.

C-MANNOSIDE COMPOUNDS USEFUL FOR THE TREATMENT OF URINARY TRACT INFECTIONS

This application is a Continuation of International Application No. PCT/IB2019/055806, filed 8 Jul. 2019, which claims the benefit of U.S. Provisional Application No. 62/695,993, filed 10 Jul. 2018 and U.S. Provisional Application No. 62/755,588, filed 5 Nov. 2018, which are incorporated herein by reference in their entireties.

FIELD OF THE INVENTION

Disclosed herein are new C-mannoside compounds and compositions and their application as pharmaceuticals for the treatment of human disease. Methods of inhibition of FimH activity in a human subject are also provided for the treatment diseases such as urinary tract infection.

BACKGROUND OF THE INVENTION

Urinary tract infection (UTI) is one of the most common infectious diseases in women. The morbidity and economic impact are enormous, with over $2.5 billion spent annually on treatment. Further, recurrent infections are a significant problem despite appropriate antibiotic therapy of the initial infection case. Women who present with an initial episode of acute UTI have a 25-44% chance of developing a second and a 3% chance of experiencing three episodes within six months of the initial UTI. Furthermore, resistance to antibiotics commonly prescribed to treat or prevent UTI is spreading rapidly among uropathogens, highlighting the need for new antibiotic-sparing and -enabling therapies.

Greater than 85% of UTI are caused by uropathogenic *Escherichia coli* (UPEC). Gram-negative bacteria such as UPEC are the causative agents of a wide variety of acute and chronic infectious diseases. Many of these infections are initiated by a critical interaction between host ligands (frequently polysaccharide moieties) and bacterial adhesins (frequently expressed at the distal tip of polymeric pilus fibers assembled by the chaperone-usher pathway). Animal models of UTI have revealed that the mannose-binding FimH adhesin of type 1 pili is critical for the colonization of and invasion into the bladder epithelium by UPEC, as well as other uropathogenic members of the Enterobacteriaceae family, such as *Klebsiella, Enterobacter*, and *Citrobacter* species.

Type 1 pili are anchored in the bacterial outer membrane and are largely composed of repeating FimA protein subunits which form a helically wound cylinder that comprises the thick pilus rod. The distal FimH adhesin protein is connected to the the pilus rod by the flexible tip fibrillum, which is composed of one copy each of FimF and FimG. The adhesin tip protein FimH is a two-domain protein comprised of a pilin domain (FimH$_P$), which allows it to incorporate into the pilus, and a lectin domain (FimHL) that contains a conserved mannose binding pocket. The X-ray crystal structure of FimH bound to mannose showed that mannose is bound in a negatively charged pocket on FimH. The mannose binding site is highly conserved as it is invariant in 300fimH genes sequenced from clinical UPEC strains. It is the interaction of FimH with mannosylated host proteins that is believed to mediate colonization of the lower urinary tract by UPEC and other Enterobacteriaceae during UTI.

To elucidate the molecular details of UPEC pathogenesis, several murine models of infection have been established which recapitulate many of the clinical manifestations often seen in humans. These models include acute UPEC infections, chronic and/or recurrent infections, and catheter-associated UTI. In all of these models the adhesin FimH has been shown to play an integral role in pathogenesis, highlighting it as an excellent therapeutic target. The fundamental interaction between FimH and the host is believed to occur with binding to high-mannose containing glycans, such as uroplakins and other proteins expressed on the surface of bladder epithelial cells, that coat the luminal surface of the bladder. This initial binding facilitates bacterial colonization of the bladder epithelium and invasion of the bacteria into the bladder epithelial cells. Once internalized, a single bacterium that escapes into the host cell cytoplasm can rapidly replicate and progress to form a biofilm-like intracellular bacterial community (IBC). Once these communities reach maturation they are able to disperse and escape from the cell, filamenting to evade neutrophil phagocytosis. These filamentous bacteria can then go on to infect neighboring cells, reinitiating IBC formation and the pathogenic cycle. Importantly, evidence of IBCs and bacterial filaments has been observed in the urine of women suffering with an acute UTI, supporting the validity of the mouse model in recapitulating human disease.

In contrast to UTI, which is primarily mediated by a bacterial pathogen, the disease manifested in patients suffering from idiopathic inflammatory bowel disease (IBD), such as Crohn's disease (CD) and ulcerative colitis (UC), is the result of a complex interplay between a genetically susceptible host, a dysfunctional immune system, and a microbial component. Examination of biopsied tissue from patients suffering from CD and UC has highlighted an increase in the abundance of *E. coli* associated with gut mucosa. Analysis of these bacteria has resulted in discovery of a distinct pathotype known as adherent and invasive *E. coli* (AIEC), though a portion of these strains appear similar genomically to UPEC. Identification of AIEC and their putative role in CD and UC has led to a number of follow up studies by several independent groups examining the intestinal microbiota in patients with IBD. This work has provided substantial evidence for the overgrowth of AIEC in ileal CD patients, with less convincing data for other IBD subtypes, including UC, colonic CD, and ileocolonic CD. Analysis of ileal enterocytes isolated from CD patients identified abnormal expression of the host receptor carcinoembryonic antigen-related cell adhesion molecule 6 (CEACAM6), which is highly mannosylated and been demonstrated to facilitate binding of AIEC to these cells via type 1 pili. Interestingly, adherence and invasion of AIEC into intestinal epithelial cells leads to increased expression of the receptor CEACAM6, suggesting AIEC are able to promote their own colonization of the ileum in CD patients. Utilization of a transgenic mouse expressing human CEA family gene cluster, including CEACAM6, results in increased colonization of AIEC, which recapitulates many of the clinical symptoms of CD including severe colitis, weight loss, and in this model decreased survival. Furthermore, these symptoms can be completely abolished through the administration of an anti-CEACAM6 antibody or through the genetic deletion of FimH in the bacterial strain, demonstrating a direct link between the recognition of CECAM6 by FimH and disease progression. Therefore, therapies targeting FimH among AIEC could have great benefit in relieving symptoms in CD patients.

SUMMARY OF THE INVENTION

Novel compounds and pharmaceutical compositions, which have been found to inhibit FimH have been discovered, together with methods of synthesizing and using the compounds including methods for the treatment of FimH-mediated diseases in a patient by administering the compounds.

More specifically, in one embodiment, the present invention relates to a compound of formula I, or a pharmaceutically acceptable salt thereof:

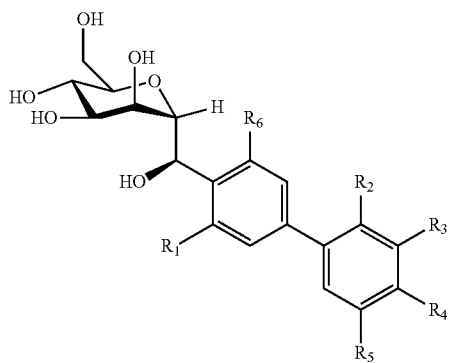

I in which $R_1$ is $CH_3$, $CF_3$, or Cl;

$R_2$ is F, Cl, OR', or H;

$R_3$, $R_4$, and $R_5$ are independently H, F, Cl, Br, $C_{3-6}$cycloalkyl, OR', —$N(C_{1-6}alkyl)_2$, $C_{2-6}$ alkenyl, $C_{2-6}$ alkynyl, $C_{1-6}$ alkyl (optionally substituted with up to seven fluorine atoms, up to one hydroxy, up to one —$N(C_{1-6}alkyl)_2$, and up to one —$OC_{1-6}alkyl$); provided not all $R_3$, $R_4$, and $R_5$ are hydrogen simultaneously.

$R_6$ is H or F;

R' is independently H or $C_{1-6}$ alkyl optionally substituted with up to seven fluorine atoms;

In an embodiment, $R_1$ is $CH_3$ or $CF_3$.
In an embodiment, $R_1$ is $CH_3$.
In an embodiment, $R_2$ is H.
In an embodiment, $R_3$ is F or $CF_3$.
In an embodiment, $R_4$ is $CH_3$, Cl, Br, vinyl, $CF_3$, F, or H.
In an embodiment, $R_4$ is H.
In an embodiment, $R_5$ is F or H.
In an embodiment, $R_5$ is F.
In an embodiment, $R_6$ is H.
In an embodiment, $R_1$ is $CH_3$ or $CF_3$; $R_2$ is H; $R_3$ is F; $R_4$ is $CH_3$, Cl, Br, vinyl, $CF_3$, F, or H; $R_5$ is F or H; and $R_6$ is H.

In an embodiment the compound is (2R,3S,4S,5S,6R)-2-((R)-(3',5'-Difluoro-3,4'-dimethyl-[1,1'-biphenyl]-4-yl)(hydroxy)methyl)-6-(hydroxymethyl)tetrahydro-2H-pyran-3,4,5-triol.

In an embodiment the compound is (2R,3S,4S,5S,6R)-2-((R)-(4'-Chloro-3',5'-difluoro-3-methyl-[1,1'-biphenyl]-4-yl)(hydroxy)methyl)-6-(hydroxymethyl)tetrahydro-2H-pyran-3,4,5-triol.

In an embodiment the compound is (2R,3S,4S,5S,6R)-2-((R)-(4'-Bromo-3',5'-difluoro-3-methyl-[1,1'-biphenyl]-4-yl)(hydroxy)methyl)-6-(hydroxymethyl)tetrahydro-2H-pyran-3,4,5-triol.

In an embodiment the compound is (2R,3S,4S,5S,6R)-2-((R)-(3',5'-Difluoro-3-methyl-4'-vinyl-[1,1'-biphenyl]-4-yl)(hydroxy)methyl)-6-(hydroxymethyl)tetrahydro-2H-pyran-3,4,5-triol.

In an embodiment the compound is (2R,3S,4S,5S,6R)-2-((R)-(3'-Fluoro-3-methyl-4'-(trifluoromethyl)-[1,1'-biphenyl]-4-yl)(hydroxy)methyl)-6-(hydroxymethyl)tetrahydro-2H-pyran-3,4,5-triol.

In an embodiment the compound is (2R,3S,4S,5S,6R)-2-((R)-(3'-Fluoro-3-methyl-5'-(trifluoromethyl)-[1,1'-biphenyl]-4-yl)(hydroxy)methyl)-6-(hydroxymethyl)tetrahydro-2H-pyran-3,4,5-triol.

In an embodiment the compound is (2R,3S,4S,5S,6R)-2-((R)-Hydroxy(3',4',5'-trifluoro-3-methyl-[1,1'-biphenyl]-4-yl)methyl)-6-(hydroxymethyl)tetrahydro-2H-pyran-3,4,5-triol.

In an embodiment the compound is (2R,3S,4S,5S,6R)-2-((R)-(3',5'-Difluoro-3-(trifluoromethyl)-[1,1'-biphenyl]-4-yl)(hydroxy)methyl)-6-(hydroxymethyl)tetrahydro-2H-pyran-3,4,5-triol.

In an embodiment the compound is (2R,3S,4S,5S,6R)-2-((R)-(3',5'-Difluoro-3-methyl-[1,1'-biphenyl]-4-yl)(hydroxy)methyl)-6-(hydroxymethyl)tetrahydro-2H-pyran-3,4,5-triol.

In another embodiment, the present invention relates to use as a medicament of a compound of formula I or a pharmaceutically acceptable salt.

In another embodiment, the present invention provides a compound of formula I or a pharmaceutically acceptable salt thereof for use in therapy.

In another embodiment, the present invention relates to use of a compound of formula I or a pharmaceutically acceptable salt in the treatment of urinary tract infection (UTI).

In another embodiment, the present invention provides a compound of formula (I) or a pharmaceutically acceptable salt thereof for use in of a disease or condition ameliorated by the inhibition of FimH function or activity.

In another embodiment, the present invention provides a compound of formula (I) or a pharmaceutically acceptable salt thereof for use in the treatment or prevention of UTI.

In another embodiment, the present invention relates to use of a compound of formula I or a pharmaceutically acceptable salt in the manufacture of a medicament for the prevention or treatment of a disease or condition ameliorated by the inhibition of FimH function or activity.

In another embodiment, the present invention provides use of a compound of formula I or a pharmaceutically acceptable salt in the manufacture of a medicament for the prevention or treatment of UTI.

In another embodiment, the present invention relates to a pharmaceutical composition comprising a compound of formula I or a pharmaceutically acceptable salt together with a pharmaceutically acceptable carrier.

In another embodiment, the present invention relates to a method of treatment of a FimH-mediated disease comprising the administration of a therapeutically effective amount of a compound of formula I or a pharmaceutically acceptable salt to a human patient in need thereof.

In another embodiment, the present invention relates to the method of treating a bacterial infection, Crohn's disease (CD), or Inflammatory Bowel Disease (IBD) with a compound of formula I or a pharmaceutically acceptable salt.

In another embodiment, the present invention provides a method for the treatment of urinary tract infection (UTI) comprising the administration of a therapeutically effective amount of a compound of formula I or a pharmaceutically acceptable salt to a human patient in need thereof.

In an embodiment, said bacterial infection is a urinary tract infection (UTI).

In an embodiment, said urinary tract infection is recurrent.

In an embodiment, said urinary tract infection is chronic.

In an embodiment, said bacterial infection is an antibiotic-resistant bacterial infection.

In an embodiment, said disease is Crohn's disease.

In an embodiment, said disease is Inflammatory Bowel Disease.

In an embodiment, said pharmaceutical composition is formulated for oral (PO) administration.

In an embodiment, said composition is chosen from a tablet and a capsule.

In an embodiment, said pharmaceutical composition is formulated for topical administration.

In another embodiment, the present invention relates to a method of treating a FimH-mediated disease comprising the step of administering:
 a. a therapeutically effective amount of a compound of formula I or a pharmaceutically acceptable salt thereof, and
 b. another therapeutic agent.

In another embodiment, the present invention relates to a combination of a compound of formula I or a pharmaceutically acceptable salt and another therapeutic agent.

DETAILED DESCRIPTIONS

Definitions

The term "$C_{1-6}$ alkyl," as used herein, alone or in combination, refers to a straight-chain or branched-chain alkyl radical containing from 1 to 6 carbon atoms. Examples of $C_{1-6}$ alkyl radicals include methyl (Me), ethyl (Et), n-propyl, isopropyl, n-butyl, isobutyl, sec-butyl, tert-butyl, pentyl, iso-amyl, hexyl, and the like.

The term "$C_{3-6}$cycloalkyl," as used herein, alone or in combination, refers to a saturated monocyclic alkyl group wherein each cyclic moiety contains from 3 to 6 carbon atom ring members. Examples are cyclopropyl (cPr), cyclopentyl (cPe), cyclobutyl (cBu), and cyclohexyl (cHex).

The term "$C_{2-6}$alkenyl", as used herein, refers to straight or branched hydrocarbon chains containing 2 to 6 carbon atoms, and at least one carbon-carbon double bonds. Examples include ethenyl (or ethenylene) and propenyl (or propenylene).

The term "$C_{2-6}$alkynyl", as used herein, refers to straight or branched hydrocarbon chains containing 2 to 6 carbon atoms and at least one carbon-carbon triple bonds. Examples include ethynyl (or ethynylene) and propynyl (or propynylene).

The term "optionally substituted" means the anteceding group may be substituted or unsubstituted with the groups which follow. For example, "$C_{1-6}$alkyl (optionally substituted with up to seven fluorine atoms, up to one hydroxy, up to one —N($C_{1-6}$alkyl)$_2$, and up to one —O$C_{1-6}$alkyl)" include groups such as —$CF_3$, —$CF_2CF_3$, —$CH_2NMe_2$, —$CH_2OMe$, —$CHF_2$, —CHOHMe, etc.

Asymmetric centers may exist in the compound of formula I. It should be understood, that the present invention covers the compounds of absolute configuration as shown in formula I. Because of their potential use in medicine, the salts of the compounds of formula I are preferably pharmaceutically acceptable salts. Thus, reference to salts are pharmaceutically acceptable salts. Pharmaceutically acceptable' refers to those compounds (including salts), materials, compositions, and dosage forms which are, within the scope of sound medical judgment, suitable for use in contact with the tissues of human beings and animals without excessive toxicity, irritation, or other problem or complication, commensurate with a reasonable benefit/risk ratio. Suitable pharmaceutically acceptable salts include those described by Berge, Bighley and Monkhouse J. Pharm. Sci (1977) 66, pp 1-19, or those listed in P H Stahl and C G Wermuth, editors, Handbook of Pharmaceutical Salts; Properties, Selection and Use, Second Edition Stahl/Wermuth: Wiley-VCH/VHCA, 2011 (see http://www.wiley.com/WileyCDA/WileyTitle/productCd-3906390519.html).

When a compound of the invention is a base (contains a basic moiety), a desired salt form may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, g-hydroxybutyrates, glycollates, tartrates mandelates, and sulfonates, such as xylenesulfonates, methanesulfonates, propanesulfonates, naphthalene-1-sulfonates and naphthalene-2-sulfonates.

If an inventive basic compound is isolated as a salt, the corresponding free base form of that compound may be prepared by any suitable method known to the art, including treatment of the salt with an inorganic or organic base, suitably an inorganic or organic base having a higher pKa than the free base form of the compound.

When a compound of the invention is an acid (contains an acidic moiety), a desired salt may be prepared by any suitable method known to the art, including treatment of the free acid with an inorganic or organic base, such as an amine (primary, secondary, or tertiary), an alkali metal or alkaline earth metal hydroxide, or the like. Illustrative examples of suitable salts include organic salts derived from amino acids such as glycine and arginine, ammonia, primary, secondary, and tertiary amines, and cyclic amines, such as ethylene diamine, dicyclohexylamine, ethanolamine, piperidine, morpholine, and piperazine, as well as inorganic salts derived from sodium, calcium, potassium, magnesium, manganese, iron, copper, zinc, aluminum, and lithium.

Certain of the compounds of this invention may form salts with one or more equivalents of an acid (if the compound contains a basic moiety) or a base (if the compound contains an acidic moiety). The present invention includes within its scope all possible stoichiometric and non-stoichiometric salt forms.

Because the compounds of this invention may contain both acid and base moieties, pharmaceutically acceptable salts may be prepared by treating these compounds with an alkaline reagent or an acid reagent, respectively. Accordingly, this invention also provides for the conversion of one pharmaceutically acceptable salt of a compound of this invention, e.g., a hydrochloride salt, into another pharmaceutically acceptable salt of a compound of this invention, e.g., a sodium salt or a disodium salt.

Because the compounds of the present invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing more pure forms used in the pharmaceutical compositions.

The term "combination" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"FimH inhibitor" or "FimH antagonist", is used herein to refer to a compound that exhibits an HAI (hemagglutination inhibition assay) titer or EC>90 with respect to FimH function/activity of no more than about 100 µM and more typically not more than about 50 µM, as measured in the FimH hemagglutination assay (HA) described generally herein. "HAI titer or EC>90" is that concentration of the FimH inhibitor/antagonist which reduces the bacterial agglutination of guinea pig red blood cells by greater than 90%. Certain compounds disclosed herein have been discovered to exhibit inhibition of this FimH function/activity. In certain embodiments, compounds will exhibit an EC>90 with respect to FimH of no more than about 10 µM; in further embodiments, compounds will exhibit an EC>90 with respect to FimH of no more than about 1 µM; in yet further embodiments, compounds will exhibit an EC>90 with respect to FimH of not more than about 250 nM; in yet further embodiments, compounds will exhibit an EC>90 with respect to FimH of not more than about 100 nM in yet further embodiments, compounds will exhibit an EC>90 with respect to FimH of not more than about 50 nM in yet further embodiments, compounds will exhibit an EC>90 with respect to FimH of not more than about 10 nM, as measured in the FimH assay described herein.

The phrase "therapeutically effective" is intended to qualify the amount of active ingredients used in the treatment of a disease or disorder or on the effecting of a clinical endpoint. As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

As used herein, reference to "prevention" of a patient is intended to include prophylaxis. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

While it may be possible for the compounds of the subject invention to be administered as the raw chemical, it is also possible to present them as a pharmaceutical formulation (or alternatively referred to as pharmaceutical compositions). Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "therapeutically acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal, inhalation, intranasal, and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

As used herein, the term "compound(s) of the invention" means a compound of formula I in any form, i.e., any salt or non-salt form (e.g., as a free acid or base form, or as a pharmaceutically acceptable salt thereof) and any physical form thereof (e.g., including non-solid forms (e.g., liquid or semi-solid forms), and solid forms (e.g., amorphous or crystalline forms, specific polymorphic forms, solvates, including hydrates (e.g., mono-, di- and hemi-hydrates)), and mixtures of various forms.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth. The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the rectum, lung, vaginal cavity, ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg. In one embodiment, a compound of the present invention is administered around 150 mg qd (once a day) or bid (twice a day).

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for urinary tract infection involving administration of one of the compounds described herein, increased therapeutic benefit may result by also providing the patient with another therapeutic agent for urinary tract infection. In any case, regardless of the disease, disorder or condition being treated, the overall benefit experienced by the patient may simply be additive of the two therapeutic agents or the patient may experience a synergistic benefit.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating FimH-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of FimH-mediated disorders.

Specific diseases to be treated by the compounds, compositions, and methods disclosed herein include bacterial infections, Crohn's Disease, and irritable bowel syndrome (IBS). In certain embodiments, the bacterial infection is a urinary tract infection.

Besides being useful for human treatment, certain compounds and formulations disclosed herein may also be useful for veterinary treatment of companion animals, exotic animals and farm animals, including mammals, and the like. More preferred animals include horses, dogs, and cats.

General Synthetic Schemes for Examples

The compounds of the present invention can be made following the synthetic methods or obvious variants thereof described in WO2017/156508. However, without limiting the present invention in any way, the below descriptions also provide reaction methods which can be employed to make compounds of the present invention.

Four general schemes (A-D) are used for synthesis of the compounds described in the Examples below. All of them utilize Suzuki coupling between a mannoside substituted with an aryl bromide (or boronate) and an aryl boronate ester (or aryl halide). The mannosides are protected with acetyl or benzyl groups. Acetyl groups are removed with NaOMe, benzyl groups are removed with $BCl_3$ or hydrogenolysis with Pd/C.

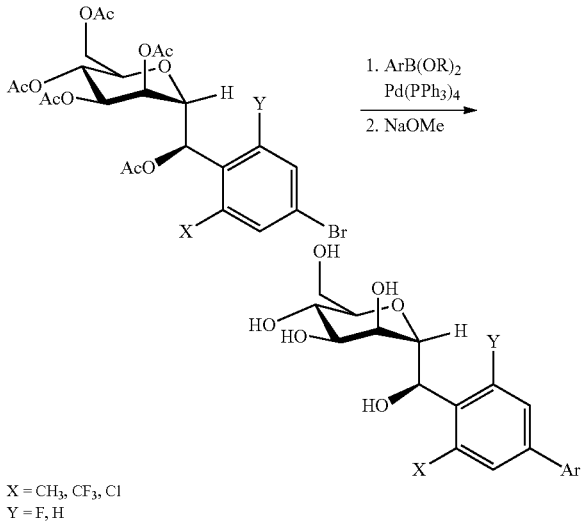

Scheme A

X = $CH_3$, $CF_3$, Cl
Y = F, H

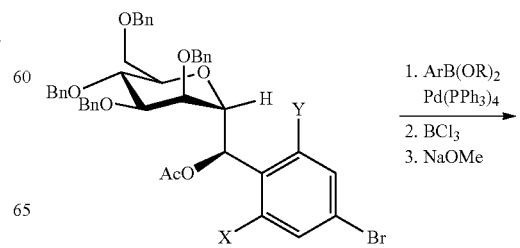

Scheme B

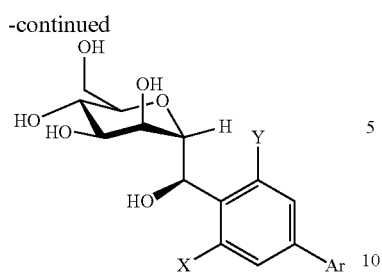

X = CH₃, CF₃, Cl
Y = F, H

Scheme C

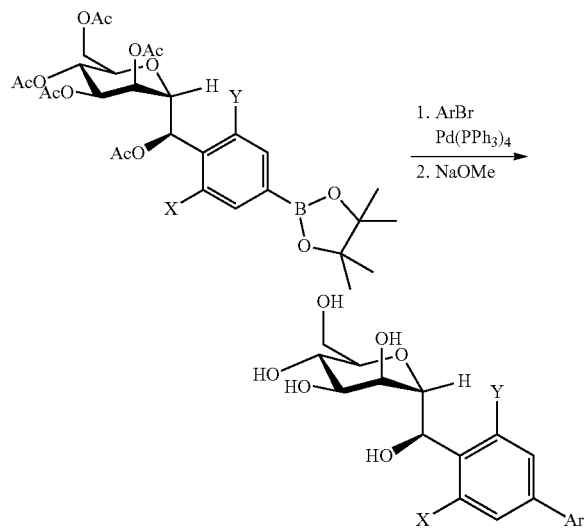

X = CH₃, CF₃, Cl
Y = F, H

Scheme D

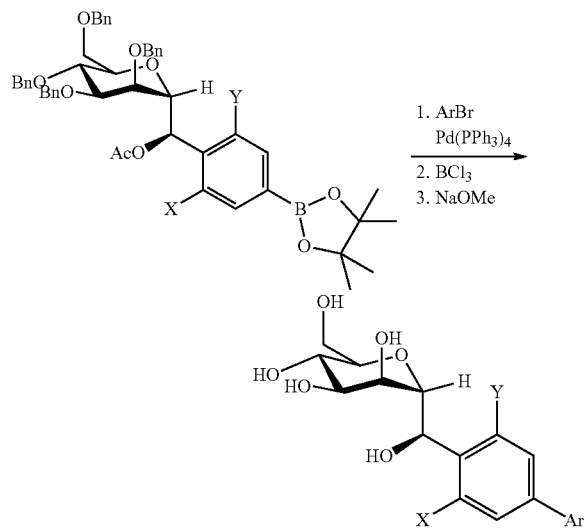

X = CH₃, CF₃, Cl
Y = F, H

General procedure for the Suzuki Coupling reactions: To a solution of mannoside (1.0 equiv.) in dioxane/water (V/V=5/1) are added aryl boronic acid (or boronate) or aryl halide (~1.1 equiv.), cesium carbonate (~3 equiv.) and tetrakis(triphenylphosphine)palladium (~0.05 equiv.) at rt. The resulting mixture is degassed three times. The flask is then placed in an oil bath preheated to 80° C., and allowed to stir for the time specified (typically 30 min to 2 h). The reaction mixture is then cooled to rt and solvents are evaporated under reduced pressure. The crude residue is then purified by silica gel chromatography. The product is then deprotected by either protocol A or B.

Deprotection protocol A: Unless specified otherwise, acetate protecting groups are removed by dissolving the partially purified mannoside from the Suzuki reaction into MeOH, and cooling to 0° C. [1M] Sodium methoxide in MeOH is added dropwise until a pH of 9-10 is achieved. After 5 min, the ice bath is removed and the reaction mixture is stirred for the time specified. Upon completion, the reaction is quenched with water or 1N HCl. and concentrated under reduced pressure. The crude product is purified by Prep-HPLC with different conditions.

Deprotection protocol B: Unless specified otherwise, benzyl ethers are deprotected by adding BCl₃ (8.0 equiv, 1M in DCM) to a solution of the partially purified mannoside from the Suzuki reaction in DCM (10 mL) at −78° C. The reaction is stirred for the time specified at −78° C. After completion, the reaction is quenched by MeOH (1 mL) at −78° C. Then the reaction is warmed to rt and concentrated under reduced pressure to afford the debenzylated compound. The acetyl group is then removed by the method described in protocol A.

C-Mannoside Building Block Synthesis:

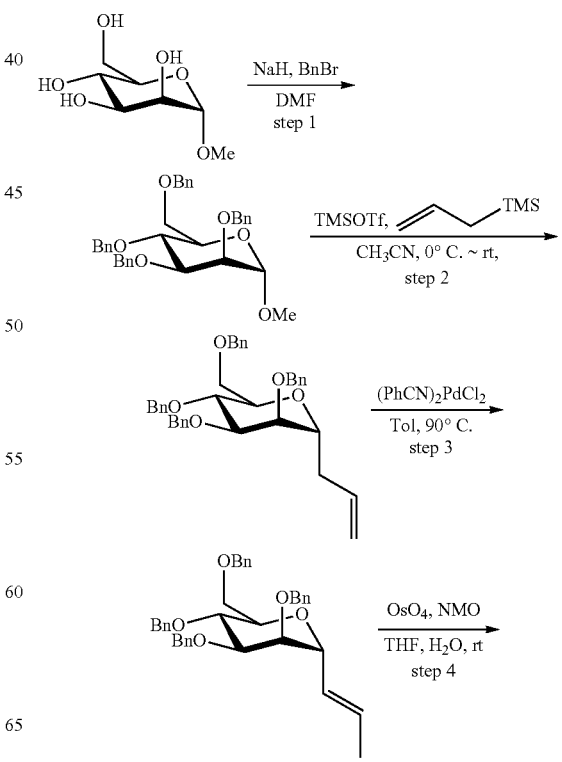

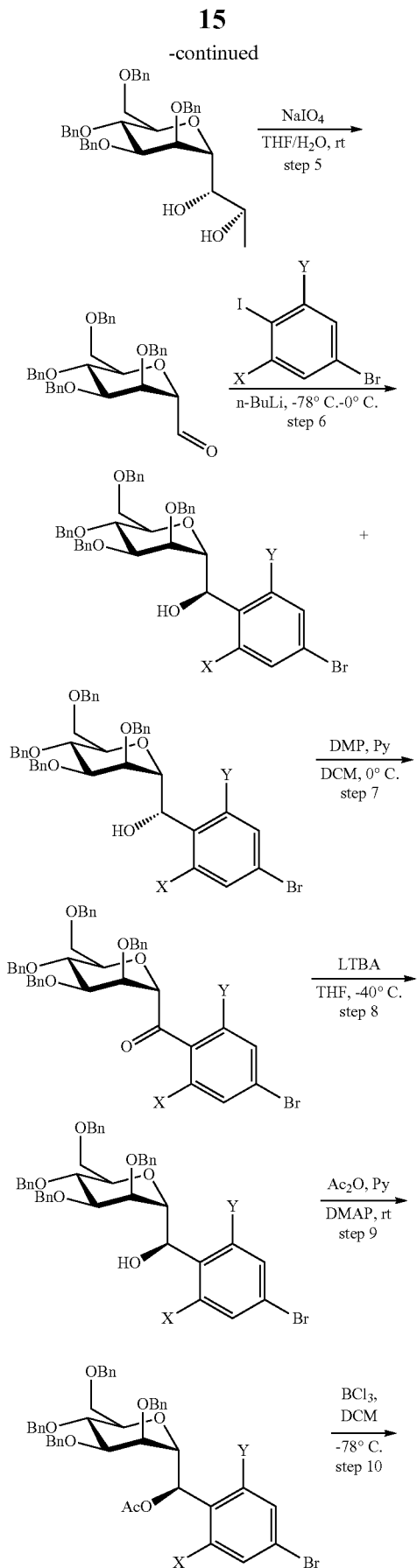

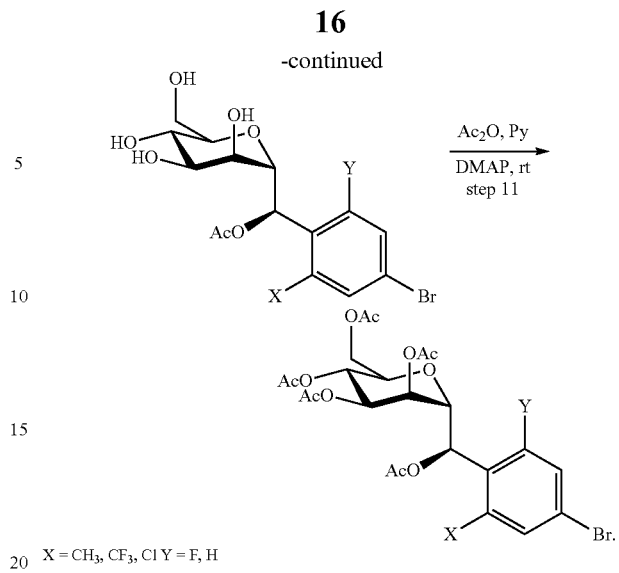

X = CH₃, CF₃, Cl  Y = F, H

The intermediates used in the preparation of the Example compounds were prepared using the general steps above which are described more specifically below.

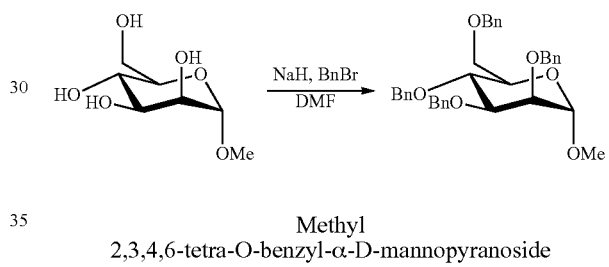

Methyl 2,3,4,6-tetra-O-benzyl-α-D-mannopyranoside

To a stirred solution of commercially available methyl α-D-mannopyranoside (30.0 g, 0.15 mol) in dry DMF (1000 mL) cooled with an ice-water bath, NaH (37.1 g, 0.93 mol, 60% in mineral oil) is added portion-wise. After addition, the reaction mixture is stirred at this temperature until the evolution of gas subsides (typically within 30 min), and it is then warmed to rt for 2 h. Benzyl bromide (158.7 g, 0.92 mol) is added to the reaction mixture. After addition, the reaction mixture is stirred at this temperature for 48 hours, at which time TLC analysis indicates that the reaction is complete. The reaction mixture is carefully poured into ice water (2500 mL) while stirring, and the resulting mixture is extracted with DCM (2500 mL×3). The combined organic layer is washed with brine, dried over anhydrous sodium sulfate and evaporated on a rotary evaporator to afford an oily residue, which is purified by silica gel chromatography, eluting with EtOAc in petroleum ether (0~20%) to give the pure compound (71.0 g, 83% yield) as a colorless oil.

Formula: $C_{35}H_{38}O_6$ Exact Mass; 554.27, Molecular Weight: 554.67.

Analytical data: ESI-MS [M+Na]⁺ calcd for ($C_{35}H_{38}O_6Na^+$) 577.27, found 577.0.

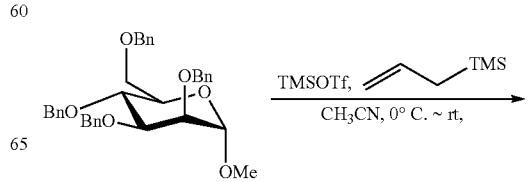

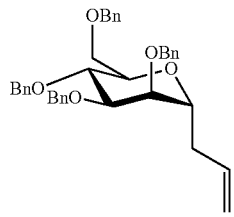

(2R,3R,4R,5R,6R)-2-Allyl-3,4,5-tris(benzyloxy)-6-((benzyloxy)methyl)tetrahydro-2H-pyran To a stirred solution of methyl 2,3,4,6-tetra-O-benzyl-α-D-mannopyranoside (78.0 g, 0.14 mol) in dry ACN (300 mL) cooled with an ice-water bath, allytrimethylsilane (33.0 g, 0.29 mol) and trimethylsilyl trifluoromethanesulfonate (16.0 g, 0.07 mol) are added dropwise. After addition, the reaction mixture is stirred at rt overnight. After completion, the reaction mixture is carefully poured into ice water (200 mL) while stirring, and the resulting mixture is extracted with EtOAc (300 mL×3). The combined organic layer is washed with brine (200 mL), dried over anhydrous sodium sulfate, and filtered. The filtrate is evaporated on a rotary evaporator to afford an oily residue, which is purified by silica gel chromatography, eluting with EtOAc in petroleum ether (1-6%) to give the pure desired product (68.0 g, 86% yield) as a yellow oil.

Formula: $C_{37}H_{40}O_5$ Exact Mass; 564.29, Molecular Weight: 564.71.

Analytical data: ESI-MS $[M+Na]^+$ calcd for $(C_{37}H_{40}O_5Na^+)$ 587.29, found 587.30.

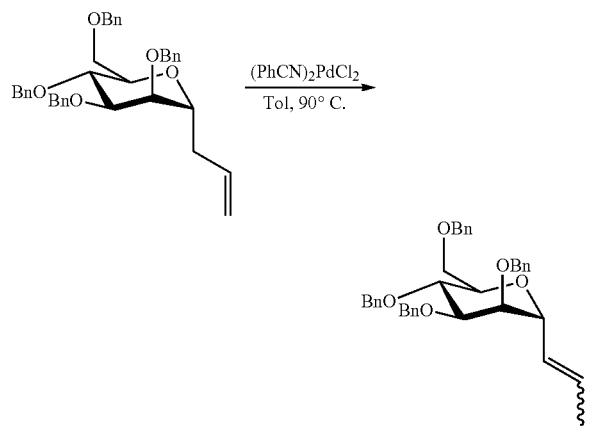

(2R,3R,4R,5R,6R)-3,4,5-Tris(benzyloxy)-2-((benzyloxy)methyl)-6-(prop-1-en-1-yl)tetrahydro-2H-pyran Pd(PhCN)$_2$Cl$_2$ (7.0 g, 0.018 mmol) is added to a solution of (2R,3R,4R,5R,6R)-2-allyl-3,4,5-tris(benzyloxy)-6-((benzyloxy)methyl)tetrahydro-2H-pyran (68.0 g, 0.12 mol) dissolved in dried toluene (350 mL) under a nitrogen atmosphere. The resulting mixture is heated at 90° C. overnight under N$_2$ atmosphere. After completion, the reaction is cooled to rt and concentrated under reduced pressure. The residue is purified by silica gel chromatography, eluting with a gradient of EtOAc in petroleum ether to give the desired product (48.0 g, 71% yield, mixture of cis and trans isomers) as a yellow oil.

Formula: $C_{37}H_{40}O_5$ Exact Mass; 564.29, Molecular Weight: 564.71.

Analytical data: MS (ESI+) calcd for $(C_{37}H_{40}O_5Na^+)$ $[M+Na]^+$ 587.29, found 587.30.

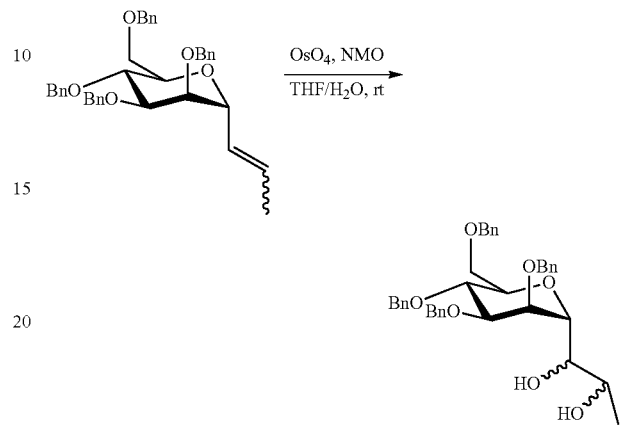

1-((2R,3S,4S,5R,6R)-3,4,5-Tris(benzyloxy)-6-(benzyloxymethyl)-tetrahydro-2H-pyran-2-yl)propane-1,2-diol OsO$_4$ (5 g, in 70 mL t-BuOH) is added to a solution of (2R,3R,4R,5R,6R)-3,4,5-tris(benzyloxy)-2-((benzyloxy)methyl)-6-(prop-1-en-1-yl)tetrahydro-2H-pyran (48 g, 0.085 mol) and 4-methylmorpholine N-oxide (39.8 g, 0.34 mol) in a mixed system of THF/water (100 mL/100 mL) at rt. The resulting mixture is stirred overnight at rt. The reaction mixture is poured into saturated aq. Na$_2$S$_2$O$_3$ solution (300 mL) and extracted with EtOAc (300 mL×3), dried over Na$_2$SO$_4$ and filtered. The filtrate is concentrated under vacuum to give a residue which is purified by silica gel chromatography, eluting with EtOAc in DCM (10~20%) to afford the desired product (34.0 g, 67% yield, mixture of isomers) as a white solid.

Formula: $C_{37}H_{42}O_7$ Exact Mass; 598.29, Molecular Weight: 598.73.

Analytical data: $^1$H-NMR (300 MHz, Chloroform-d) δ 7.42-7.12 (m, 20H), 4.66-4.36 (m, 7H), 4.08-3.93 (m, 3H), 3.92-3.85 (m, 2H), 3.83-3.68 (m, 2H), 3.64-3.58 (m, 2H), 3.52-3.44 (m, 1H), 1.25-1.17 (m, 3H). MS (ESI+) calcd for $(C_{37}H_{42}O_7Na^+)$ $[M+Na]^+$ 621.29, found 621.30.

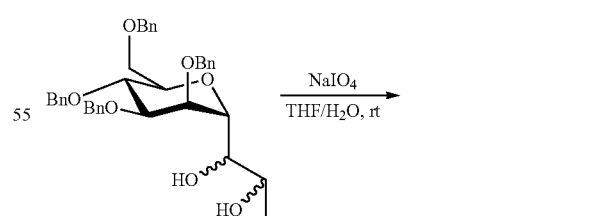

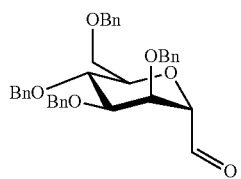

(2S,3S,4S,5R,6R)-3,4,5-Tris(benzyloxy)-6-((benzyloxy)methyl)tetrahydro-2H-pyran-2-carbaldehyde To a solution of 1-((2R,3S,4S,5R,6R)-3,4,5-tris(benzyloxy)-6-benzyloxymethyl)-tetrahydro-2H-pyran-2-yl)propane-1,2-diol (13.0 g, 21.7 mmol) in THF/water (120 mL/120 mL), NaIO$_4$ (13.0 g, 60.75 mmol) is added and the reaction mixture is stirred under N$_2$ for 3 h at rt. Upon completion, the reaction is quenched with ice water (100 mL) and extracted with DCM (250 mL×3). The combined organic layer is washed with brine (100 mL), dried over Na$_2$SO$_4$ and filtered. The filtrate is concentrated under reduced pressure to give the desired product (12.9 g, crude) which is used directly for the next step without further purification.

Formula: C$_{35}$H$_{36}$O$_6$ Exact Mass: 552.25, Molecular Weight: 552.66.

Analytical data: ESI-MS [M+Na]$^+$ calcd for (C$_{35}$H$_{36}$NaO$_6$Na$^+$) 575.24, found 575.20.

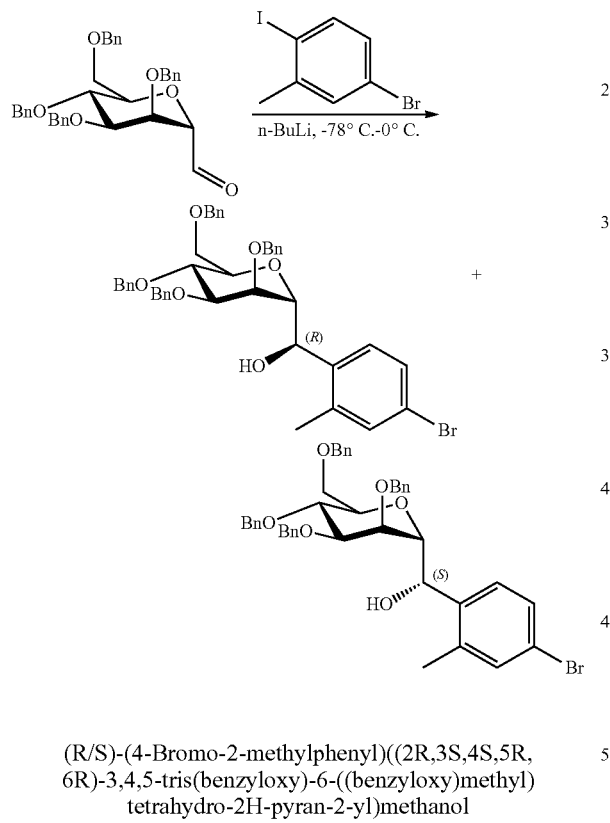

(R/S)-(4-Bromo-2-methylphenyl)((2R,3S,4S,5R,6R)-3,4,5-tris(benzyloxy)-6-((benzyloxy)methyl)tetrahydro-2H-pyran-2-yl)methanol Standard procedure: Into a flask of 150 mL of Et$_2$O at −78° C. under N$_2$, 4-bromo-1-iodo-2-methylbenzene (22.6 g, 76.1 mmol) in anhydrous Et$_2$O (10 mL) is added. Then n-BuLi in hexanes (2.5 M, 26 mL, 65 mmol) is added dropwise at −78° C. and stirred for an additional hour. Then, freshly prepared crude (2S,3S,4S,5R,6R)-3,4,5-tris(benzyloxy)-6-((benzyloxy)methyl)tetrahydro-2H-pyran-2-carbaldehyde (12.0 g, 21.7 mmol) dissolved in Et$_2$O (90 mL) is added via cannula over a period of 5 minutes. The mixture is stirred at −78° C. for 30 min, and then slowly warmed to 0° C. over a period of 1.5 h. The reaction mixture is quenched with saturated aq. NH$_4$Cl and extracted with EtOAc (250 mL×3). The combined organic phase is washed with brine (100 mL), dried over Na$_2$SO$_4$ and filtered. The filtrate is concentrated under reduced pressure and the residue is purified by silica gel chromatography DCM/EtOAc/petroleum ether to give (R)-(4-bromo-2-methylphenyl)((2R,3S,4S,5R,6R)-3,4,5-tris(benzyloxy)-6-((benzyloxy)methyl)tetrahydro-2H-pyran-2-yl)methanol (4.0 g, 25% yield for two steps) as a light yellow oil and (S)-(4-bromo-2-methylphenyl)((2R,3S,4S,5R,6R)-3,4,5-tris(benzyloxy)-6-((benzyloxy)methyl)tetrahydro-2H-pyran-2-yl)methanol (8.0 g, 51% yield for two steps) as a light yellow oil.

(R) isomer:
Formula: C$_{42}$H$_{43}$BrO$_6$ Exact Mass: 722.22 Molecular Weight: 723.69

Analytical data for 1R: $^1$H NMR (300 MHz, CDCl$_3$) δ 7.41-7.28 (m, 21H), 7.18-7.13 (m, 2H), 5.08 (d, J=5.1 Hz, 1H), 4.71 (d, J=11.7 Hz, 1H), 4.64-4.56 (m, 3H), 4.49 (s, 2H), 4.40 (s, 2H), 4.28-4.21 (m, 1H), 4.18-4.13 (m, 1H), 4.10 (t, J=5.1 Hz, 1H), 3.99-3.94 (m, 1H), 3.89 (t, J=5.9 Hz, 1H), 3.83-3.70 (m, 2H), 3.49 (br. s., 1H), 2.29 (s, 3H). ESI-MS [M+Na+] calcd for (C$_{42}$H$_{43}$BrO$_6$Na) found: 745.5 (100%), 747.5 (97.3%).

(S) isomer:
Formula: C$_{42}$H$_{43}$BrO$_6$ Exact Mass: 722.22 Molecular Weight: 723.69

Analytical data for 1S: $^1$H NMR (300 MHz, CDCl$_3$) δ 7.37-7.16 (m, 23H), 5.06 (d, J=5.5 Hz, 1H), 4.73-4.67 (m, 1H), 4.62-4.44 (m, 7H), 4.11-4.03 (m, 2H), 3.85-3.76 (m, 3H), 3.73-3.67 (m, 2H), 3.19 (br. s., 1H), 2.18 (s, 3H). ESI-MS [M+Na]$^+$ calcd for C$_{42}$H$_{43}$BrO$_6$Na$^+$ 745.21, found 745.5 (100%), 747.5 (97.3%).

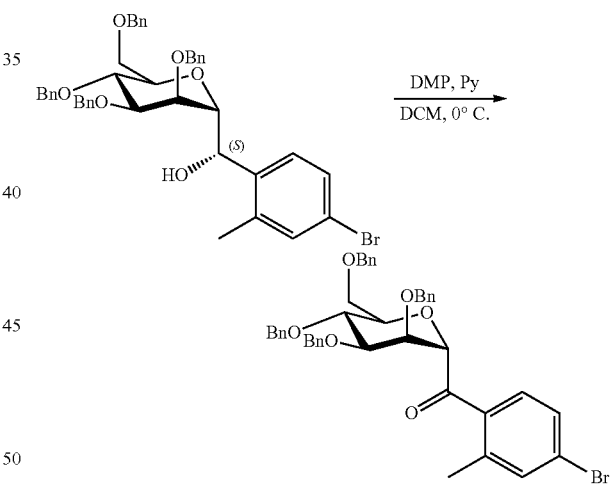

(4-Bromo-2-methylphenyl)((2S,3S,4S,5R,6R)-3,4,5-tris(benzyloxy)-6-((benzyloxy)methyl)tetrahydro-2H-pyran-2-yl)methanone To a stirred solution of (S)-(4-bromo-2-methylphenyl)((2R,3S,4S,5R,6R)-3,4,5-tris(benzyloxy)(benzyloxy)methyl)tetrahydro-2H-pyran-2-yl)methanol (2.9 g, 0.004 mol) in dry DCM (200 mL), dry pyridine (0.79 g, 0.01 mol) is added under N$_2$ at 0° C. Dess-Martin periodinane (3.4 g, 0.008 mol) is added portion-wise, and the reaction mixture is kept at 0° C. for 1 hour, and then it is allowed to warm to 15° C. over an additional 1.5 hours. The reaction flask is cooled in an ice bath, and a 1:1 mixture of a 10% solution of Na$_2$S$_2$O$_3$ (30 mL) and a saturated aq. NaHCO$_3$ (30 mL)

is added, and the reaction is stirred for 5 min at rt. The layers are then separated and the aqueous layer is extracted with DCM (20 mL×3). The organic fractions are combined and washed with the solution of NaHCO$_3$, then separated, dried over Na$_2$SO$_4$, and concentrated in vacuo without heating and purified by silica gel chromatography, eluting with EtOAc in petroleum ether (12%) to afford the ketone (2.03 g, 70%) as a yellow oil (2.03 g, 70%, crude).

Formula: C$_{42}$H$_{41}$BrO$_6$ Exact Mass; 720.21, Molecular Weight: 721.68.

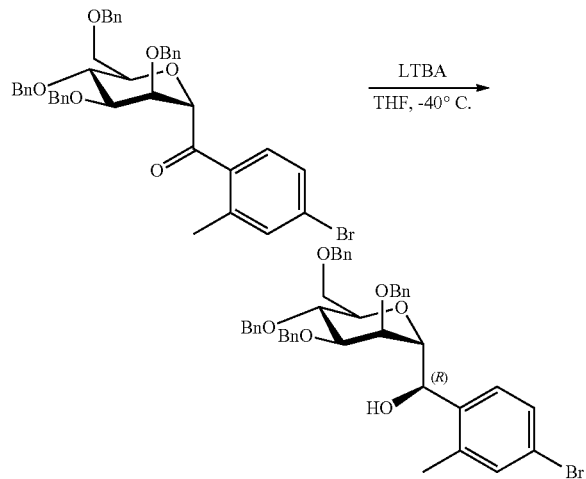

(R)-(4-Bromo-2-methylphenyl)((2R,3S,4S,5R,6R)-3,4,5-tris(benzyloxy)-6-((benzyloxy)methyl)tetrahydro-2H-pyran-2-yl)methanol To a stirred solution of (4-bromo-2-methylphenyl)((2S,3S,4S,5R,6R)-3,4,5-tris(benzyloxy)-6-((benzyloxy)methyl)tetrahydro-2H-pyran-2-yl)methanone (2.03 g, 2.8 mmol) in dried THF (200 mL), LTBA (8.2 mL, 8.2 mmol, 1M solution in THF) is added under N$_2$ at −40° C. The mixture is warmed to 0° C. and stirred an additional 1 h. When TLC analysis indicates that the reaction is completed, the reaction mixture is diluted with EtOAc (400 mL). A solution of saturated aq. potassium sodium tartrate (200 mL) is added, and the mixture is vigorously stirred for 1 h at rt. The organic layer is separated and the aqueous layer is extracted with EtOAc (2×100 mL), the combined organic layers are dried over Na$_2$SO$_4$, filtered and the filtrate is concentrated under vacuum. The residue is purified by silica gel chromatography DCM/EtOAc/petroleum ether to afford the desired isomer 1R (1.62 g, 80% yield) as a yellow oil.

Analytical data—as reported above.

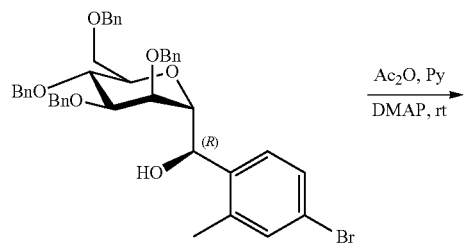

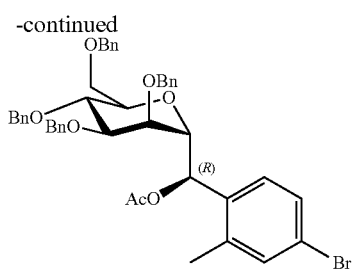

(R)-(4-Bromo-2-methylphenyl)((2R,3S,4S,5R,6R)-3,4,5-tris(benzyloxy)-6-((benzyloxy)methyl)tetrahydro-2H-pyran-2-yl)methyl acetate Dimethylaminopyridine (21 mg, 0.17 mmol) and (R)-(4-bromo-2-methylphenyl)((2R,3S,4S,5R,6R)-3,4,5-tris(benzyloxy)-6-((benzyloxy)methyl)tetrahydro-2H-pyran-2-yl)methanol (2.45 g, 3.4 mmol) are dissolved in dry pyridine (10 mL) under N$_2$. Acetic anhydride (518 mg, 5.08 mmol) is added dropwise within 5 min. After stirring for 1 h at rt, the reaction mixture is cooled to 0° C. and quenched with MeOH (2 mL) and solvents are evaporated in vacuo. The residue is re-dissolved in DCM (30 mL) and washed successively with water (30 mL), 1 N aq. HCl (30 mL×2), and water (30 mL), and then dried over Na$_2$SO$_4$ and filtered. The filtrate is concentrated under reduced pressure and the residue is purified by silica gel chromatography, eluting with EtOAc in petroleum ether (0-20%) to afford the desired product 3 (2.5 g, 96% yield) as a yellow oil.

Formula: C$_{44}$H$_{45}$BrO$_7$ Exact Mass; 764.23, Molecular Weight: 765.73.

Analytical data: $^1$H-NMR (300 MHz, Chloroform-d) δ 7.32-7.24 (m, 14H), 7.23-7.14 (m, 8H), 7.02 (d, J=8.2 Hz, 1H), 6.06 (d, J=6.9 Hz, 1H), 4.73 (d, J=11.1 Hz, 1H), 4.61-4.30 (m, 7H), 4.25 (dd, J=6.9 Hz, 3.7 Hz, 1H), 3.99-3.82 (m, 2H), 3.78-3.52 (m, 4H), 2.31 (s, 3H), 1.85 (s, 3H). ESI-MS [M+Na]$^+$ calcd for (C$_{44}$H$_{45}$BrO$_7$Na$^+$) 787.22, found 787 &789

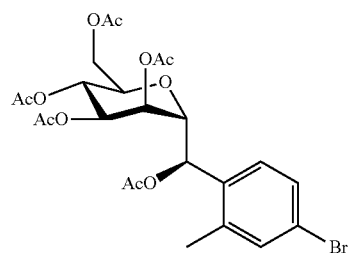

(2R,3R,4S,5R,6R)-2-((R)-Acetoxy(4-bromo-2-methylphenyl)methyl)-6-(acetoxymethyl)tetrahydro-2H-pyran-3,4,5-triyltriacetate (R)-(4-bromo-2-methylphenyl)((2R,3S,4S,5R,6R)-3,4,5-tris(benzyloxy)-6-((benzyloxy)methyl)tetrahydro-2H-pyran-2-yl)methylacetate (340 mg, 0.44 mmol) is dissolved in dry DCM (15 mL) under N$_2$, and the reaction mixture is cooled to −78° C. Boron trichloride (3.56 mL, 1M in DCM, 3.56 mmol) is added dropwise, and the reaction mixture is stirred for 30 min. Upon completion, the reaction is quenched by the addition of MeOH (2 mL). The reaction mixture is concentrated in vacuo and the residue is purified by silica gel chromatography (MeOH/DCM) to afford the debenzylated intermediate. This intermediate (~150 mg) is re-dissolved in dry pyridine (3 mL) under $N_2$, and the reaction is cooled to 0° C. Dimethylaminopyridine (2.5 mg, 0.02 mmol) is added, followed by acetic anhydride (230 mg, 2.3 mmol), and the reaction mixture is stirred for 5 min at 0° C. and then brought to r.t. After 1 h, the reaction is cooled again to 0° C., and quenched with MeOH (2 mL). Solvents are removed in vacuo, and the residue is then re-dissolved in DCM (25 mL) and washed successively with water (10 mL), 1 N aq. HCl (10 mL×2), and water (10 mL). The organic layer is separated, dried over $Na_2SO_4$ and filtered. The filtrate is concentrated in vacuo and the residue is purified by silica gel chromatography, eluting with EtOAc in petroleum ether to afford the desired product (200 mg, 79% for two steps) as a white solid.

Formula: $C_{24}H_{29}BrNaO_n$ Exact Mass; 572.09, Molecular Weight: 573.38.

Analytical data: $^1$H NMR (300 MHz, CDCl$_3$) δ ppm 7.36-7.32 (m, 2H), 7.24-7.21 (m, 1H), 6.19 (d, J=6.9 Hz, 1H), 5.54 (t, J=3.3 Hz, 1H), 5.37 (dd, $J_1$=9.0 Hz, $J_2$=3.6 Hz, 1H), 5.18 (t, J=8.5 Hz, 1H), 4.26-4.21 (m, 2H), 4.02-3.91 (m, 2H), 2.43 (s, 3H), 2.14 (s, 3H), 2.08 (s, 6H), 2.03 (s, 3H), 1.97 (s, 3H). ESI-MS [M+Na]$^+$ calcd for ($C_{24}H_{29}BrNaO_{11}Na^+$), 595.08, found 595.2 (100%), 597.3 (97.3%).

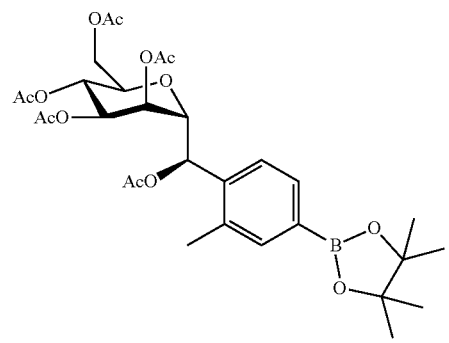

(2R,3R,4S,5R,6R)-2-((R)-Acetoxy(2-methyl-4-(4,4,5,5-tetramethyl-1,3,2-dioxaborolan-2-yl)phenyl)methyl)-6-(acetoxymethyl)tetrahydro-2H-pyran-3,4,5-triyl triacetate Under nitrogen atmosphere, a mixture of (2R,3R,4S,5R,6R)-2-(acetoxymethyl)-6-(4-bromo-2-methylbenzoyl)tetrahydro-2H-pyran-3,4,5-triyl triacetate (500 mg, 0.87 mmol), bis(pinacolato) diboron (243.5 mg, 0.96 mmol), potassium acetate (256.1 mg, 2.61 mmol) and (1.1'-bis(diphenylphosophino) ferrocene)dichloropalladium(II) dichloromethane complex (Pd(dppf)Cl$_2$.DCM) (71 mg, 0.09 mmol) in dioxane (10 mL) is heated at 90° C. with stirring for 3 h. Upon completion, the reaction is cooled to rt and concentrated under reduced pressure. The residue is purified by silica gel chromatography, eluting with EtOAc in petroleum ether (0~25%) to afford the desired product (480 mg, 89% yield) as a light yellow oil (purity 90%).

Formula: $C_{30}H_{41}BO_{13}$ Exact Mass; 620.26, Molecular Weight: 620.46.

Analytical data: $^1$H-NMR (300 MHz, Chloroform-d) δ 7.66-7.56 (m, 1H), 7.38-7.28 (m, 1H), 7.22-7.19 (m, 1H), 6.21 (dd, J=26.3 Hz, 6.8 Hz, 1H), 5.58-5.52 (m, 1H), 5.41-5.33 (m, 1H), 5.20-5.11 (m, 1H), 4.25-4.19 (m, 2H), 4.00-3.91 (m, 2H), 2.42 (d, J=7.3 Hz, 3H), 2.12 (s, 3H), 2.07-1.98 (m, 9H), 1.94 (d, J=2.8 Hz, 3H), 1.32-1.19 (m, 12H).

ESI-MS [M+H]$^+$ calcd for ($C_{30}H_{41}BO_{13}H$) 621.26, found 621.0

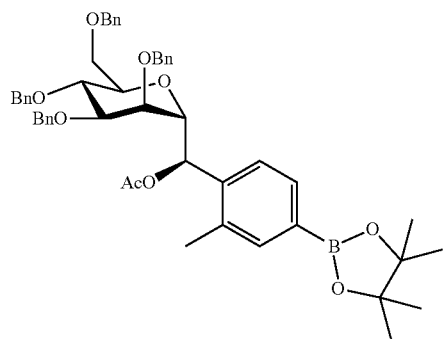

(R)-(2-Methyl-4-(4,4,5,5-tetramethyl-1,3,2-dioxaborolan-2-yl)phenyl)((2R,3S,4S,5R,6R)-3,4,5-tris(benzyloxy)-6-(benzyloxymethyl)tetrahydro-2H-pyran-2-yl)methyl acetate Under nitrogen atmosphere, a mixture of (R)-(4-bromo-2-methylphenyl)((2R,3S,4S,5R,6R)-3,4,5-tris(benzyloxy)-6-((benzyloxy)methyl)tetrahydro-2H-pyran-2-yl)methyl acetate (1.2 g, 1.57 mmol), bis(pinacolato) diboron (438 mg, 1.72 mmol), potassium acetate (462 mg, 4.71 mmol) and (1.1'-bis(diphenylphosophino)ferrocene)dichloropalladium (II)dichloromethane complex (Pd(dppf)Cl$_2$.DCM) (131 mg, 0.16 mmol) in dioxane (10 mL) is stirred for 16 h at 90° C. Upon completion, the reaction is cooled to rt, then it is concentrated under reduced pressure. The residue is purified by silica gel chromatography, eluting with EtOAc in petroleum ether (0-20%) to afford the desired boronate (920 mg, 72% yield) as a yellow oil.

Formula: $C_{50}H_{57}BO_9$ Exact Mass; 812.14, Molecular Weight: 812.79.

Analytical data: $^1$H-NMR (300 MHz, Chloroform-d) δ 7.66-7.56 (m, 1H), 7.38-7.28 (m, 1H), 7.22-7.19 (m, 1H), 6.21 (dd, J=26.3 Hz, 6.8 Hz, 1H), 5.58-5.52 (m, 1H), 5.41-5.33 (m, 1H), 5.20-5.11 (m, 1H), 4.25-4.19 (m, 2H), 4.00-3.91 (m, 2H), 2.42 (d, J=7.3 Hz, 3H), 2.12 (s, 3H), 2.07-1.98 (m, 9H), 1.94 (d, J=2.8 Hz, 3H), 1.32-1.19 (m, 12H).

ESI-MS [M+NH₄]⁺ calcd for ($C_{50}H_{57}BO_9NH_4^+$) 830.41, found 830.5.

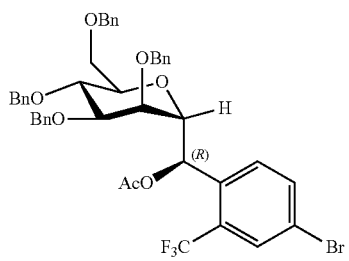

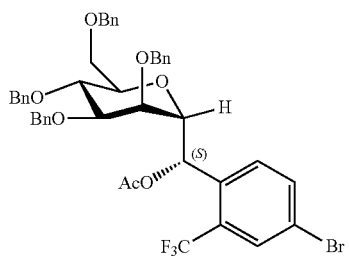

(R)-(4-Bromo-2-trifluoromethylphenyl)((2R,3S,4S, 5R,6R)-3,4,5-tris(benzyloxy)-6-((benzyloxy)methyl) tetrahydro-2H-pyran-2-yl)methyl acetate & (S)-(4-bromo-2-trifluoromethylphenyl)((2R,3S,4S,5R,6R)-3,4,5-tris(benzyloxy)-6-((benzyloxy)methyl) tetrahydro-2H-pyran-2-yl)methylacetate Following the procedure described earlier for (R)-(4-bromo-2-methylphenyl)((2R,3S,4S,5R,6R)-3,4,5-tris(benzyloxy)-6-((benzyloxy)methyl)tetrahydro-2H-pyran-2-yl)methanol, 4-bromo-1-iodo-2-(trifluoromethyl)benzene (6.24 g, 18 mmol) is treated with n-BuLi and reacted with (2S, 3S,4S,5R,6R)-3,4,5-tris(benzyloxy)-6-((benzyloxy)methyl) tetrahydro-2H-pyran-2-carbaldehyde (3.3 g, 6.0 mmol). It is purified by combiflash chromatography (Phase A: petroleum ether; phase B: DCM/EtOAc/petroleum ether (20/1/2), Flow rate:80 mL/min; Gradient 30% B-70% B over 60 min. The (R)-alcohol is eluted at 30 min and the (S)-alcohol is eluted at 50 min) affording the (R)-alcohol (1.2 g, assumed, 26% for two steps) as a light yellow oil and the (S)-alcohol (1.2 g, assumed, 26% for two steps) as a light yellow oil. Following the acetylation procedure described previously for (R)-(4-bromo-2-methylphenyl)((2R,3S,4S,5R,6R)-3,4, 5-tris(benzyloxy)-6-((benzyloxy)methyl)tetrahydro-2H-pyran-2-yl)methyl acetate, the (S)-alcohol (1.1 g) is protected to afford the (S)-acetate (1.1 g, 95%) and the (R)-alcohol (1.1 g) is protected to afford the (R)-acetate (1.2 g, 99%).

Formula: $C_{44}H_{42}BrF_3O_7$ Exact Mass: 818.21 Molecular Weight: 819.7.

Analytical data for (R)-isomer: ¹H NMR (300 MHz, DMSO-d₆) δ 7.86 (d, J=1.8 Hz, 1H), 7.77-7.66 (m, 2H), 7.33-7.17 (m, 20H), 6.20 (d, J=6.3 Hz, 1H), 4.65 (d, J=11.4 Hz, 1H), 4.54-4.49 (m, 4H), 4.43-4.37 (m, 1H), 4.33-4.25 (m, 3H), 4.03-4.00 (m, 1H), 3.89-3.86 (m, 1H), 3.77-3.72 (m, 2H), 3.61-3.45 (m, 2H), 1.92 (s, 3H). ESI-MS [M+Na]⁺ calcd for ($C_{44}H_{42}BrF_3O_7Na^+$) 841.20, found 841.40, 843.40.

Analytical data for (S)-isomer: ¹H NMR (300 MHz, DMSO-d₆) δ 7.87 (d, J=1.8 Hz, 1H), 7.74-7.62 (m, 2H), 7.36-7.20 (m, 20H), 6.28 (d, J=6.0 Hz, 1H), 4.60-4.56 (m, 4H), 4.52 (s, 1H), 4.39 (d, J=12.0 Hz, 1H), 4.22-4.18 (m, 2H), 4.11-3.99 (m, 3H), 3.85-3.82 (m, 1H), 3.69-3.66 (m, 1H), 3.58-3.52 (m, 1H), 3.42-3.37 (m, 1H), 1.96 (s, 3H). ESI-MS [M+Na]+ calcd for ($C_{44}H_{42}BrF_3O_7Na^+$) [M+Na]⁺ 841.20, found 841.0.

Example 1

(2R,3S,4S,5S,6R)-2-((R)-(3',5'-Difluoro-3,4'-dimethyl-[1,1'-biphenyl]-4-yl)(hydroxy)methyl)-6-(hydroxymethyl)tetrahydro-2H-pyran-3,4,5-triol

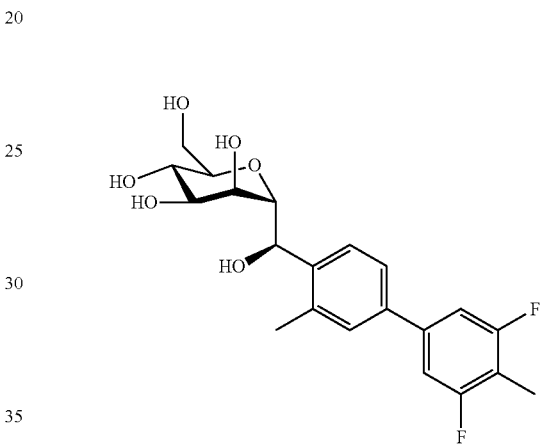

Following Scheme D, (R)-(2-methyl-4-(4,4,5,5-tetramethyl-1,3,2-dioxaborolan-2-yl)phenyl)((2R,3S,4S,5R,6R)-3, 4,5-tris(benzyloxy)-6-((benzyloxy)methyl)tetrahydro-2H-pyran-2-yl)methyl acetate (200 mg, 0.25 mmol) and 5-bromo-1,3-difluoro-2-methylbenzene (56 mg, 0.27 mmol) are reacted via the standard Suzuki coupling procedure (1 h at 80° C.), followed by deprotection protocol B (BCl₃, 1M in DCM, 60 min at −78° C.) and followed by deprotection protocol A (1 h at rt), and then purification by Prep-HPLC with conditions: XBridge Prep C18 OBD Column 19×150 mm 5 um; Mobile Phase A:Water (10 mmol/L NH₄HCO₃), Mobile Phase B: ACN; Flow rate: 20 mL/min; Gradient: 27% B to 50% B in 7 min; 254 nm; Rt: 6.23 min provides the title compound (30 mg, 30% yield for three steps) as a white solid.

Formula: $C_{21}H_{24}F_2O_6$. Exact Mass: 410.15, Molecular Weight: 410.41.

Analytical data: ¹H NMR (300 MHz, Methanol-d₄) δ 7.62 (d, J=8.1 Hz, 1H), 7.51-7.41 (m, 2H), 7.22-7.19 (m, 2H), 5.24 (d, J=6.7 Hz, 1H), 4.25 (t, J=2.8 Hz, 1H), 4.10 (dd, J=6.8 Hz, 2.6 Hz, 1H), 4.07-4.03 (m, 1H), 3.80-3.62 (m, 4H), 2.50 (s, 3H), 2.23 (s, 3H). ESI-MS [M+NH₄]⁺ calc'd for ($C_2H_{24}F_2O_6NH_4^+$) 428.19, found 428.20.

Example 2

(2R,3S,4S,5S,6R)-2-((R)-(4'-Chloro-3',5'-difluoro-3-methyl-[1,1'-biphenyl]-4-yl)(hydroxy)methyl)-6-(hydroxymethyl)tetrahydro-2H-pyran-3,4,5-triol

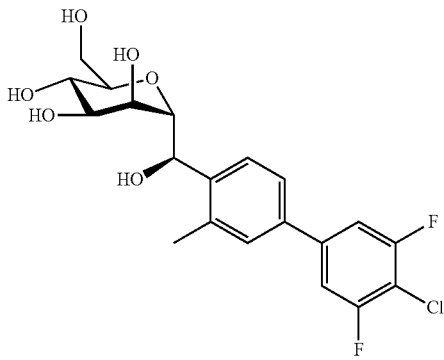

Following Scheme D,(R)-(2-methyl-4-(4,4,5,5-tetramethyl-1,3,2-dioxaborolan-2-yl)phenyl)((2R,3S,4S,5R,6R)-3,4,5-tris(benzyloxy)-6-((benzyloxy)methyl)tetrahydro-2H-pyran-2-yl)methyl acetate (200 mg, 0.25 mmol) and 5-bromo-2-chloro-1,3-difluorobenzene (67 mg, 0.29 mmol) is reacted via the standard Suzuki coupling procedure (40 min at 80° C.), followed by deprotection protocol B (BCl$_3$, 1M in DCM, 40 min at −78° C.) and followed by deprotection protocol A (40 min at 0° C.). Purification of the residue by Prep-HPLC with conditions: XBridge Prep OBD C18 Column 30×150 mm 5 um; Mobile Phase A: water (10 mmol/L NH$_4$HCO$_3$), Mobile Phase B: ACN; Flow rate: 60 mL/min; Gradient: 5% B to 65% B in 1 min; 254 nm; Rt: 6.17 min affords the title compound (41.0 mg, 39% yield for three steps) as a white solid.

Formula: C$_{20}$H$_{21}$ClF$_2$O$_6$ Exact Mass: 430.10 Molecular Weight: 430.83

Analytical Data: $^1$H NMR (300 MHz, Methanol-d$_4$) δ $^1$H NMR (300 MHz, Methanol-d$_4$) δ 7.64 (d, J=8.2 Hz, 1H), 7.54-7.38 (m, 4H), 5.25 (d, J=6.7 Hz, 1H), 4.23 (t, J=2.8 Hz 1H), 4.10 (dd, J=6.7, 2.6 Hz, 1H), 4.05-4.02 (m, 1H), 3.74-3.62 (m, 4H), 2.51 (s, 3H). ESI-MS [M+Na]$^+$ Calc'd for (C$_{20}$H$_{21}$ClF$_2$O$_6$Na$^+$), 453.09, found 453.10.

Example 3

(2R,3S,4S,5S,6R)-2-((R)-(4'-Bromo-3',5'-difluoro-3-methyl-[1,1'-biphenyl]-4-yl)(hydroxy)methyl)-6-(hydroxymethyl)tetrahydro-2H-pyran-3,4,5-triol

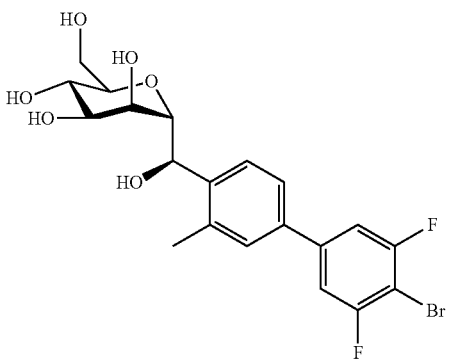

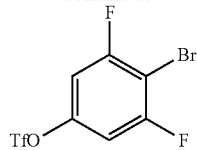

4-Bromo-3,5-difluorophenyl trifluoromethanesulfonate To a solution of 4-bromo-3,5-difluorophenol (300 mg, 1.44 mmol) in THF (5 mL) is added NaOtBu (276 mg, 2.9 mmol) and PhN(SO$_2$CF$_3$)$_2$ (569 mg, 1.6 mmol) at 25° C. The resulting mixture is stirred at 25° C. for 3 h. The reaction is quenched with water (10 mL), extracted with EtOAc (20 mL×3), and dried over Na$_2$SO$_4$. The solvent is concentrated under reduced pressure, and the residue purified by silica gel chromatography, eluting with EtOAc in petroleum ether (0-10%) to give 4-bromo-3,5-difluorophenyl trifluoromethanesulfonate (120 mg, 25% yield) as a colorless oil.

Formula: C$_7$H$_2$BrF$_5$O$_3$S Exact Mass; 339.88, Molecular Weight: 341.05.

MS (ESI+) [M+H]$^+$ calcd for (C$_7$H$_2$BrF$_5$O$_3$SH$^+$) 340.89, no MS signal.

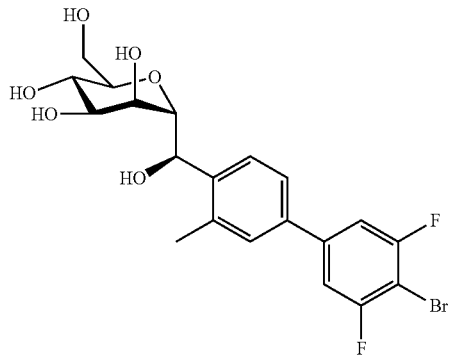

(2R,3S,4S,5S,6R)-2-((R)-(4'-Bromo-3',5'-difluoro-3-methyl-[1,1'-biphenyl]-4-yl)(hydroxy)methyl)-6-(hydroxymethyl)tetrahydro-2H-pyran-3,4,5-triol Following Scheme D, (R)-(2-methyl-4-(4,4,5,5-tetramethyl-1,3,2-dioxaborolan-2-yl)phenyl)((2R,3S,4S,5R,6R)-3,4,5-tris(benzyloxy)-6-((benzyloxy)methyl)tetrahydro-2H-pyran-2-yl)methyl acetate (200 mg, 0.25 mmol) and 4-bromo-3,5-difluorophenyl trifluoromethanesulfonate (100 mg, 0.29 mmol) is reacted via the standard Suzuki coupling procedure (2 h at 80° C.), followed by deprotection protocol B (BCl$_3$, 1M in DCM, 60 min at −78° C.) and followed by deprotection protocol A (1 h at rt). Purification of the residue by Prep-HPLC with conditions: Column: XBridge Shield RP 18 OBD Column 30×150 mm 5 um; Mobile Phase A: Water (10 mmol/L NH$_4$HCO$_3$), Mobile Phase B: ACN; Flow rate: 60 mL/min; Gradient: 5% B to 60% B in 7 min; 254 nm; Rt: 6.50 min affords title compound (24 mg, 20% yield for three steps) as a white solid.

Formula: C$_{20}$H$_{21}$BrF$_2$O$_6$. Exact Mass: 474.05. Molecular Weight: 475.28.

Analytical data: $^1$H NMR (400 MHz, Methanol-d$_4$) δ 7.65 (d, J=8.2 Hz, 1H), 7.55-7.48 (m, 2H), 7.43-7.37 (m, 2H), 5.25 (d, J=6.7 Hz, 1H), 4.23 (t, J=2.9 Hz, 1H), 4.10 (dd, J=6.7 Hz, 2.6 Hz, 1H), 4.06-4.03 (m, 1H), 3.76-3.60 (m, 4H), 2.52 (s, 3H). ESI-MS [M+NH$_4$]$^+$ calc'd for (C$_{20}$H$_{21}$BrF$_2$O$_6$NH$_4$$^+$) 492.08, found 492.05.

Example 4

(2R,3S,4S,5S,6R)-2-((R)-(3',5'-Difluoro-3-methyl-4'-vinyl-[1,1'-biphenyl]-4-yl)(hydroxy)methyl)-6-(hydroxymethyl)tetrahydro-2H-pyran-3,4,5-triol

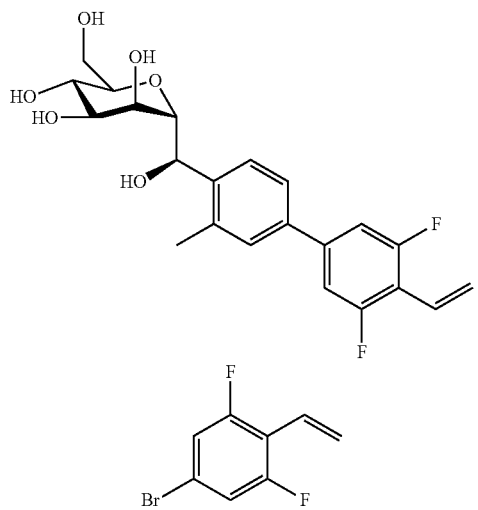

5-Bromo-1,3-difluoro-2-vinylbenzene To a solution of methyltriphenylphosphonium bromide (6.92 g, 19.4 mmol) in THF (20 mL) is added NaHMDS (17.8 mL, 1M in THF) at 0° C. under N$_2$. The resulting solution is stirred for 30 min at 0° C. Then, 4-bromo-2,6-difluorobenzaldehyde (3.0 g 13.6 mmol) is added to the above solution at 0° C. The resulting solution is stirred for 3 h at 0° C. The reaction is quenched with water (20 mL), extracted with EtOAc (20 mL×3), then dried over Na$_2$SO$_4$ and filtered. The filtrate is concentrated under reduced pressure, and the residue purified by silica gel chromatography, eluting with petroleum ether, to give the title product (1.5 g, 50%) as a yellow oil.

Formula: C$_8$H$_5$BrF$_2$ Exact Mass; 217.95, Molecular Weight: 219.03.

MS (ESI+) [M+H]$^+$ calcd for (C$_8$H$_5$BrF$_2$H$^+$) 220.04, no mass signal.

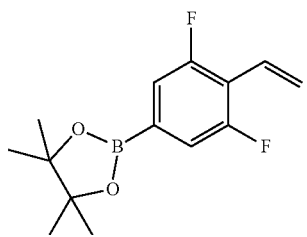 [SMILES: C=Cc1c(F)cc(B2OC(C)(C)C(C)(C)O2)cc1F]

2-(3,5-Difluoro-4-vinylphenyl)-4,4,5,5-tetramethyl-1,3,2-dioxaborolane A mixture of 5-bromo-1,3-difluoro-2-vinylbenzene (500 mg, 2.3 mmol), bis(pinacolato) diboron (640 mg, 2.5 mmol), (1.1'-bis(diphenylphosohino)ferrocene)dichloropalladium(II) dichloromethane complex (187 mg, 0.23 mmol) and KOAc (674 mg, 6.9 mmol) in dioxane (5 mL) is stirred for 12 h at 80° C. under a N$_2$ atmosphere. After completion, the reaction is cooled to 25° C. The reaction mixture is diluted with water (5 mL) and then extracted with EtOAc (10 mL×3), dried over Na$_2$SO$_4$ and filtered. The filtrate is concentrated under reduced pressure, and the residue purified by silica gel chromatography, eluting with petroleum ether to give the title product (270 mg, 44%) as a yellow oil.

Formula: C$_{14}$H$_{17}$BF$_2$O$_2$ Exact Mass; 266.13, Molecular Weight: 266.09.

MS (ESI+) [M+H]$^+$ calcd for (C$_{14}$H$_{17}$BF$_2$O$_2$H$^+$) 267.14, no mass signal.

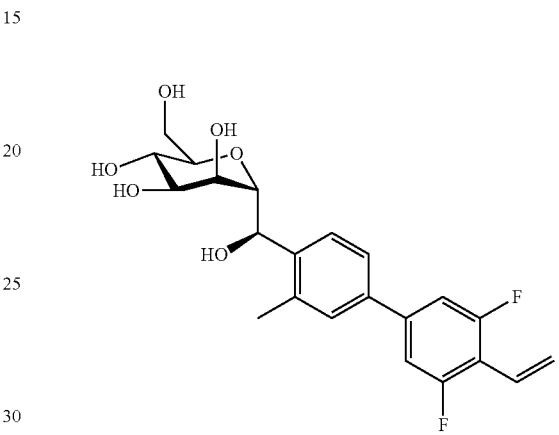

(2R,3S,4S,5S,6R)-2-((R)-(3',5'-Difluoro-3-methyl-4'-vinyl-[1,1'-biphenyl]-4-yl)(hydroxy)methyl)-6-(hydroxymethyl)tetrahydro-2H-pyran-3,4,5-triol Following Scheme B, (R)-(4-bromo-2-methylphenyl)((2R,3S,4S,5R,6R)-3,4,5-tris(benzyloxy)-6-((benzyloxy)methyl)tetrahydro-2H-pyran-2-yl)methyl acetate (200 mg, 0.26 mmol) and 2-(3,5-difluoro-4-vinylphenyl)-4,4,5,5-tetramethyl-1,3,2-dioxaborolane (80 mg, 0.3 mmol) is reacted via the standard Suzuki coupling procedure (40 min at 80° C.), followed by deprotection protocol B (BCl$_3$, 1 M in DCM, 40 min at −78° C.) and followed by deprotection protocol A (40 min at 23° C.). Purification of the residue by Prep-HPLC with conditions: Column: XBridge Shield RP18 OBD Column 30*150 mm, 5 um; Mobile Phase A: Water (0.1% formic acid), Mobile Phase B: ACN; Flow rate: 60 mL/min; Gradient: 5% B to 50% B in 10 min; 254 nm; Rt: 9.77 min) provides the title compound (30 mg, 27% yield for three steps) as a white solid.

Formula: C$_{22}$H$_{24}$F$_2$O$_6$, Exact Mass: 422.15, Molecular Weight: 422.42.

Analytical data: $^1$H NMR (300 MHz, Methanol-d$_4$) δ 7.62 (d, J=8.1 Hz, 1H), 7.55-7.42 (m, 2H), 7.27-7.25 (m, 2H), 6.82-6.72 (m, 1H), 6.04 (d, J=18.4 Hz, 1H), 5.60 (d, J=12.8 Hz, 1H), 5.23 (d, J=6.8 Hz, 1H), 4.23 (t, J=2.8 Hz, 1H), 4.09 (dd, J=2.6 Hz, 9.4 Hz, 1H), 4.05-4.00 (m, 1H), 3.73-3.66 (m, 4H), 2.50 (s, 3H). ESI-MS [M+NH$_4$]$^+$ calcd for (C$_{22}$H$_{24}$F$_2$O$_6$NH$_4$$^+$) 440.16, found 440.20.

Example 5

(2R,3S,4S,5S,6R)-2-((R)-(3'-Fluoro-3-methyl-4'-(trifluoromethyl)-[1,1'-biphenyl]-4-yl)(hydroxy)methyl)-6-(hydroxymethyl)tetrahydro-2H-pyran-3,4,5-triol

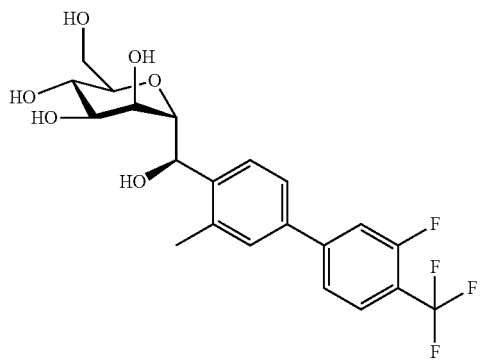

Following Scheme B, (R)-(4-bromo-2-methylphenyl)((2R,3S,4S,5R,6R)-3,4,5-tris(benzyloxy)-6-((benzyloxy)methyl)tetrahydro-2H-pyran-2-yl)methylacetate (220 mg, 0.29 mmol) and commercially available (3-fluoro-4-(trifluoromethyl) phenyl)boronic acid (72 mg, 0.35 mmol) is reacted via the standard Suzuki coupling procedure (45 min at 80° C.), followed by deprotection protocol B (BCl$_3$, 1M in DCM, 45 min at −78° C.) and deprotection protocol A (1 h at 0° C.). Purification of the residue by prep-HPLC with conditions: XBridge Prep OBD C18 Column 19×150 mm 5 um; Mobile Phase A: Water (10 mmol/L NH$_4$HCO$_3$), Mobile Phase B: ACN; Flow rate: 20 mL/min; Gradient: 25% B to 55% B in 7 min; 254/220 nm; Rt: 6.17 min affords the desired product (49.0 mg, 38% for three steps) as a white solid.

Formula: $C_{21}H_{22}F_4O_6$ Exact Mass: 446.14, Molecular Weight: 446.39.

Analytical data: $^1$H NMR (300 MHz, Methanol-d$_4$) δ 7.75 (t, J=8.0 Hz, 1H), 7.66-7.51 (m, 5H), 5.26 (d, J=6.7 Hz, 1H), 4.24 (t, J=3.0 Hz, 1H), 4.11 (dd, J=6.7 Hz, 2.6 Hz, 1H), 4.07-4.03 (m, 1H), 3.72-3.67 (m, 4H), 2.53 (s, 3H). ESI-MS [M+Na]$^+$ calc'd for ($C_{21}H_{22}F_4O_6Na^+$) 469.13, found 469.25.

Example 6

(2R,3S,4S,5S,6R)-2-((R)-(3'-Fluoro-3-methyl-5'-(trifluoromethyl)-[1,1'-biphenyl]-4-yl)(hydroxy)methyl)-6-(hydroxymethyl)tetrahydro-2H-pyran-3,4,5-triol

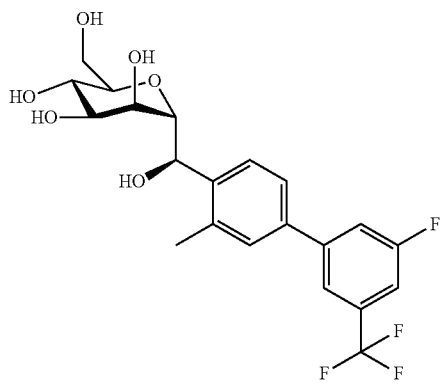

Following Scheme B, (R)-(4-bromo-2-methylphenyl)((2R,3S,4S,5R,6R)-3,4,5-tris(benzyloxy)-6-((benzyloxy)methyl)tetrahydro-2H-pyran-2-yl)methyl acetate (200 mg, 0.26 mmol) and commercially available (3-fluoro-5-(trifluoromethyl)phenyl)boronic acid (108 mg, 0.52 mmol) are reacted via the standard Suzuki coupling procedure (1.0 h at 80° C.), followed by deprotection protocol B (BCl$_3$, 1M in DCM, 1 h at −78° C.) and followed by deprotection protocol A (1 h at 25° C.). Purification of the residue by Prep-HPLC affords the desired product (40.0 mg, 34% for three steps) as a white solid.

Formula: $C_{21}H_{22}F_4O_6$ Exact Mass: 446.14, Molecular Weight: 446.39.

Analytical data: $^1$H NMR (400 MHz, Methanol-d$_4$) δ 7.75 (s, 1H), 7.70-7.67 (m, 2H), 7.55 (dd, J=8.2 Hz, 2.0 Hz, 1H), 7.51 (d, J=1.6 Hz, 1H), 7.43 (d, J=8.4 Hz, 1H), 5.27 (d, J=6.7 Hz, 1H), 4.25 (t, J=3.0 Hz, 1H), 4.11 (dd, J=6.8 Hz, 2.6 Hz, 1H), 4.06 (dd, J=8.0 Hz, 3.5 Hz, 1H), 3.74-3.64 (m, 4H), 2.53 (s, 3H). ESI-MS [M+NH$_4$]$^+$ calc'd for ($C_{21}H_{22}F_4O_6NH_4^+$) 464.17, found 464.05.

Example 7

(2R,3S,4S,5S,6R)-2-((R)-Hydroxy(3',4',5'-trifluoro-3-methyl-[1,1'-biphenyl]-4-yl)methyl)-6-(hydroxymethyl)tetrahydro-2H-pyran-3,4,5-triol

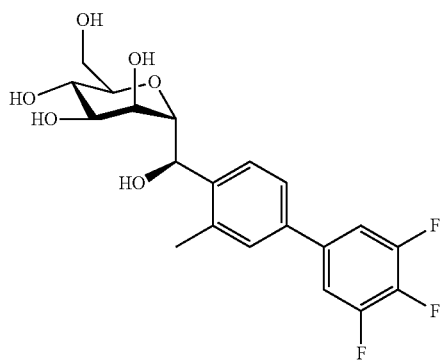

Following Scheme B, (R)-(4-bromo-2-methylphenyl)((2R,3S,4S,5R,6R)-3,4,5-tris(benzyloxy)-6-((benzyloxy)methyl)tetrahydro-2H-pyran-2-yl)methyl acetate (200 mg, 0.26 mmol) and commercially available (3,4,5-trifluorophenyl)boronic acid (91 mg, 0.52 mmol) are reacted via the standard Suzuki coupling procedure (1 h at 80° C.), followed by deprotection protocol B (BCl₃, 1M in DCM, 1 h at −78° C.) and then deprotection protocol A (1 h at 25° C.). Purification of the residue by prep-HPLC affords the desired product (25.0 mg, 23% for three steps) as a white solid.

Formula: $C_{20}H_{21}F_3O_6$ Exact Mass: 414.13, Molecular Weight: 414.37.

Analytical data: ¹H NMR (400 MHz, Methanol-d₄) δ 7.63 (d, J=8.0 Hz, 1H), 7.47 (dd, J=8.0 Hz, 2.1 Hz, 1H), 7.45-7.36 (m, 3H), 5.25 (d, J=6.7 Hz, 1H), 4.24 (t, J=3.0 Hz, 1H), 4.10 (dd, J=6.8 Hz, 2.6 Hz, 1H), 4.07-4.04 (m, 1H), 3.77-3.58 (m, 4H), 2.51 (s, 3H). ESI-MS [M+NH₄]⁺ calc'd for ($C_{20}H_{24}F_3O_6NH_4$+) 432.16, found 432.15.

Example 8

(2R,3S,4S,5S,6R)-2-((R)-(3',5'-Difluoro-3-(trifluoromethyl)-[1,1'-biphenyl]-4-yl)(hydroxy)methyl)-6-(hydroxymethyl)tetrahydro-2H-pyran-3,4,5-triol

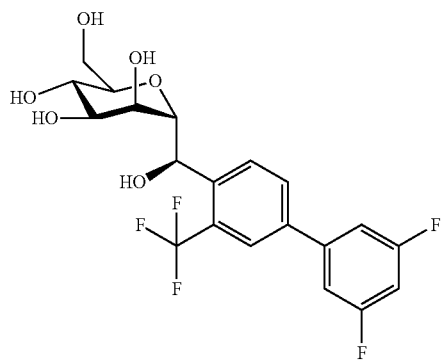

Following Scheme B, (R)-(4-bromo-2-trifluoromethylphenyl)((2R,3S,4S,5R,6R)-3,4,5-tris(benzyloxy)-6-((benzyloxy)methyl)tetrahydro-2H-pyran-2-yl)methyl acetate (200 mg, 0.24 mmol) and commercially available (3,5-difluorophenyl)boronic acid (50 mg, 0.32 mmol) are reacted via the standard Suzuki coupling procedure (1 h at 80° C.), followed by deprotection protocol B (BCl₃, 1M in DCM, 30 min at −78° C.) and then deprotection protocol A (1 h at 25° C.). Purification of the residue by Prep-HPLC (with conditions: Column: Xbridge Shield RPC18 OBD Column, 19×150 mm, 5 um; Mobile Phase A: Water (10 mmol/L NH₄HCO₃), Mobile Phase B: ACN; Flow rate: 20 mL/min; Gradient: 25% B to 50% B in 7 min; 254 nm; Rt: 5.98 min) affords the desired product (60 mg, 56% for three steps) as a white solid.

Formula: $C_{20}H_{19}F_5O_6$ Exact Mass: 450.11, Molecular Weight: 450.36.

Analytical data: ¹H NMR (400 MHz, Methanol-d₄) δ 8.02-7.90 (m, 3H), 7.39-7.27 (m, 2H), 7.05-7.00 (m, 1H), 5.38 (d, J=6.9 Hz, 1H), 4.32 (t, J=2.8 Hz, 1H), 4.19 (dd, J=6.8 Hz, 2.0 Hz, 1H), 4.02 (dd, J=8.8 Hz, 3.4 Hz, 1H), 3.75 (t, J=8.5 Hz, 1H), 3.70-3.58 (m, 3H). ESI-MS [M+NH₄]⁺ calcd for ($C_{20}H_{19}F_5O_6NH_4^+$) 468.14, found 468.20.

Example 9

(2R,3S,4S,5S,6R)-2-((R)-(3',5'-Difluoro-3-methyl-[1,1'-biphenyl]-4-yl)(hydroxy)methyl)-6-(hydroxymethyl)tetrahydro-2H-pyran-3,4,5-triol

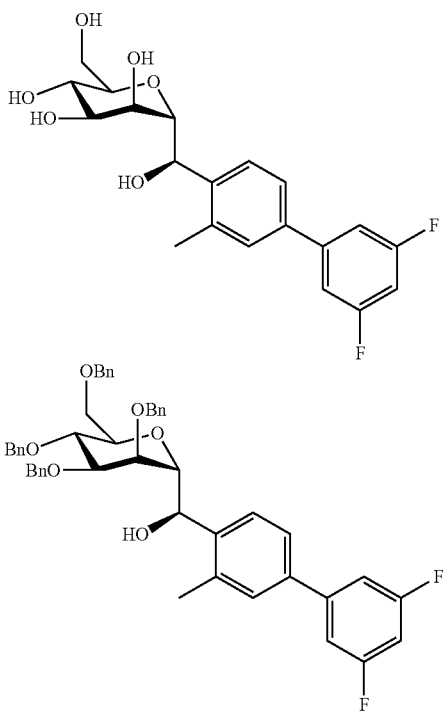

(R)-(3',5'-Difluoro-3-methyl-[1,1'-biphenyl]-4-yl)((2R,3S,4S,5R,6R)-3,4,5-tris(benzyloxy)-6-((benzyloxy)methyl)tetrahydro-2H-pyran-2-yl)methanol Into a 10-L 3-necked round-bottom flask purged and maintained with an inert atmosphere of nitrogen, is placed (R)-(4-bromo-2-methylphenyl)((2R,3S,4S,5R,6R)-3,4,5-tris(benzyloxy)-6-((benzyloxy)methyl)tetrahydro-2H-pyran-2-yl)methanol (230 g, 317 mmol, 1 equiv), Dioxane:H₂O (4:1) (2.3 L), (3,5-difluorophenyl)boronic acid (55.2 g, 349 mmol, 1.1 equiv), Cs₂CO₃ (310.6 g, 953 mmol, 3.0 equiv), and Pd(PPh₃)₄ (18.4 g, 15.9 mmol, 0.05 equiv). The resulting solution is stirred for 1 hr at 80° C. in an oil bath. The solids are filtered out. The filtrate is extracted with 3×4 L of ethyl acetate. The resulting mixture is washed with 2×4 L of saturated NaCl. The mixture is dried over anhydrous sodium sulfate and concentrated. The residue is purified by silica gel chromatography, eluting with EtOAc in petroleum ether (3%) to give 197 g (82%) of the desired product as a light yellow oil.

Formula: $C_{48}H_{46}F_2O_6$ Exact Mass: 756.33, Molecular Weight: 756.87

Analytical data: ¹H NMR (300 MHz, Chloroform-d) δ 7.52 (d, J=8.6 Hz, 1H), 7.30 (dddd, J=20.6, 8.1, 6.4, 3.9 Hz, 21H), 7.16 (dd, J=6.6, 2.9 Hz, 2H), 7.11-7.00 (m, 2H), 6.81 (tt, J=8.9, 2.4 Hz, 1H), 6.40-6.26 (m, 1H), 5.19 (d, J=5.8 Hz, 1H), 4.66 (d, J=11.6 Hz, 1H), 4.60 (d, J=4.6 Hz, 3H), 4.42 (d, J=2.4 Hz, 3H), 4.37 (d, J=11.8 Hz, 1H), 4.25-4.01 (m, 5H), 3.89-3.75 (m, 2H), 3.69 (dd, J=10.6, 4.2 Hz, 1H), 2.40 (s, 3H). ESI-MS [M+Na]+ calc'd for (C48H46F2O6Na+) 779.33, found 779.33.

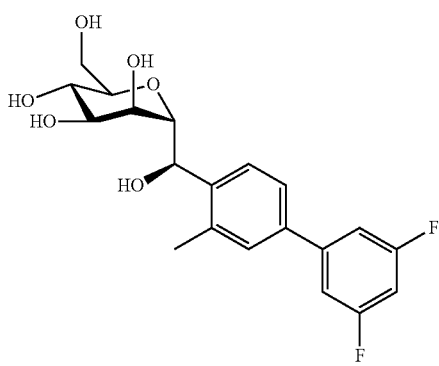

(2R,3S,4S,5S,6R)-2-((R)-(3',5'-Difluoro-3-methyl-[1,1'-biphenyl]-4-yl)(hydroxy)methyl)-6-(hydroxymethyl)tetrahydro-2H-pyran-3,4,5-triol A solution of (R)-(3',5'-difluoro-3-methyl-[1,1'-biphenyl]-4-yl)((2R,3S,4S,5R,6R)-3,4,5-tris(benzyloxy)-6-((benzyloxy)methyl)tetrahydro-2H-pyran-2-yl)methanol (1.00 g, 1.32 mmol) is prepared in methanol (20 mL, 20 volumes) by heating the two together to near reflux. The mixture is transferred to a Hastelloy high pressure reactor, cooled to RT and JM Type 10T755 (10% w/w Pd) palladium on activated carbon (100 mg, 10 wt %) is added in a single portion. This suspension is hydrogenated at 60 psig $H_2$ for 5.75 h at 45° C. The suspension is filtered through a plug of Celite which is washed with additional MeOH and the filtrate is concentrated in vacuo to afford the title compound as a grey solid (525 mg, 1.32 mmol, ~100% crude yield).

Formula: $C_{20}H_{22}F_2O_6$ Exact Mass: 396.14, Molecular Weight: 396.38

Analytical Data: 1H NMR (400 MHz, MeOH-$d_4$) δ 2.39 (s, 3H), 3.55-3.60 (m, 4H), 3.92-3.96 (m, 1H), 3.99 (dd, J=6.6, 2.4 Hz, 1H), 4.13 (t, J=2.7 Hz, 1H), 5.13 (d, J=6.8 Hz, 1H), 6.80 (tt, J=9.0, 2.2 Hz, 1H), 7.10-7.14 (m, 2H), 7.34 (s, 1H), 7.37 (d, J=8.3 Hz, 1H), 7.52 (d, J=8.1 Hz, 1-). ESI-MS [M+NH$_4$]$^+$ calc'd for ($C_{20}H_{22}F_2{}_6NH_4^+$) 414.17, found 414.15.

The following examples (compounds) in Table 1 have been prepared using the methods disclosed herein, wherein said Examples have Formula I.

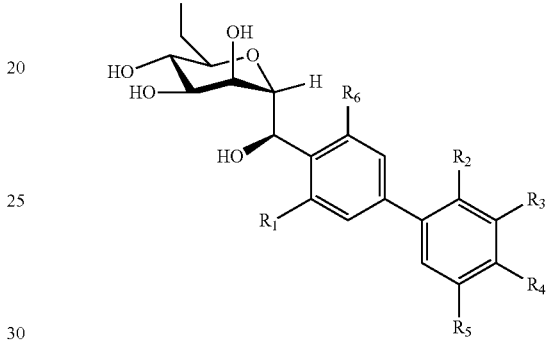

TABLE 1

| Example number | $R_1$ | $R_6$ | $R_2$ | $R_3$ | $R_4$ | $R_5$ | MS characterization |
|---|---|---|---|---|---|---|---|
| 10 | Me | H | O—iPr | H | H | Cl | ESI-MS [M + Na]$^+$ calc'd for ($C_{23}H_{29}ClO_7Na^+$) 475.91, found 475.2977 |
| 11 | Me | H | F | H | Me | Cl | ESI-MS [M + Na]$^+$ calc'd for ($C_{20}H_{22}ClFO_6Na^+$) 449.85, found 449.2958 |
| 12 | Me | H | H | Me | Cl | Me | ESI-MS [M + Na]$^+$ calc'd for ($C_{22}H_{27}ClO_6Na^+$) 445.89, found 445.3463 |
| 13 | Me | H | H | Me | OCF$_3$ | Me | ESI-MS [M + Na]$^+$ calc'd for ($C_{22}H_{25}F_3O_7Na^+$) 481.41, found 481.3141 |
| 14 | Me | H | H | Me | H | tBu | ESI-MS [M + Na]+ calc'd for ($C_{25}H_{34}O_6Na^+$) 453.52, found 453.4106 |
| 15 | Me | H | H | Cl | Cl | H | ESI-MS [M + Na]$^+$ calc'd for ($C_{20}H_{22}Cl_2O_6Na^+$) 451.07, found 451.00. |
| 16 | Me | H | H | Cl | H | Cl | ESI-MS [M + NH$_4$]$^+$ calc'd for ($C_{20}H_{22}Cl_2O_6NH_4^+$) 446.11, found 446.10. |
| 17 | Me | H | F | H | H | F | ESI-MS [M + NH$_4$]$^+$ calc'd for ($C_{20}H_{22}F_2O_6NH_4^+$) 414.17, found 414.15. |
| 18 | Me | H | F | F | H | H | ESI-MS [M + NH$_4$]$^+$ calc'd for ($C_{20}H_{22}F_2O_6NH_4^+$) 414.17, found 414.15. |
| 19 | Me | H | OH | H | Cl | Cl | ESI-MS [Mn + Na]$^+$ calc'd for ($C_{20}H_{22}Cl_2O_7Na^+$) 467.06, found 467.15. |
| 20 | Me | H | OMe | H | Cl | Cl | ESI-MS [M + Na]$^+$ calc'd for ($C_{21}H_{24}Cl_2O_7Na^+$) 481.08, found 481.20. |
| 21 | Me | H | OcPe | H | Me | H | ESI-MS [M + NH$_4$]$^+$ calc'd for ($C_{26}H_{34}O_7NH_4^+$) 476.26, found 476.20. |
| 22 | Me | H | H | F | H | Cl | ESI-MS [M + NH$_4$]$^+$ calc'd for ($C_{20}H_{22}ClFO_6NH_4^+$) 430.14, found 430.05. |
| 23 | Me | H | H | F | F | H | ESI-MS [M + NH$_4$]$^+$ calc'd for ($C_{20}H_{22}F_2O_6NH_4^+$) 414.17, found 414.15. |
| 24 | Me | H | H | OMe | H | F | ESI-MS [M + NH$_4$]$^+$ calc'd for ($C_{21}H_{25}FO_7NH_4^+$) 426.19, found 426.15. |
| 25 | Me | H | H | CF$_3$ | F | H | ESI-MS [M + NH$_4$]$^+$ calc'd for ($C_{21}H_{22}F_4O_6NH_4^+$) 464.17, found 464.05. |
| 26 | Me | H | H | CF$_3$ | H | Cl | ESI-MS [M + NH$_4$]$^+$ calc'd for ($C_{21}H_{22}ClF_3O_6NH_4^+$) 480.14, found 480.05. |
| 27 | Me | H | H | OMe | F | H | ESI-MS [M + NH$_4$]$^+$ calc'd for ($C_{21}H_{25}FO_7NH_4^+$) 426.19, found 426.10. |

TABLE 1-continued

| Example number | $R_1$ | $R_6$ | $R_2$ | $R_3$ | $R_4$ | $R_5$ | MS characterization |
|---|---|---|---|---|---|---|---|
| 28 | Me | H | H | F | $OCF_3$ | H | ESI-MS [M + NH$_4$]$^+$ calc'd for ($C_{21}H_{22}F_4O_7NH_4^+$) 480.16, found 480.05. |
| 29 | Cl | H | H | F | H | F | ESI-MS [M + Na]$^+$ calc'd for ($C_{19}H_{19}ClF_2O_6Na^+$) 439.07, found 439.30. |
| 30 | Me | H | H | $CF_3$ | Cl | H | ESI-MS [M + NH$_4$]$^+$ calc'd for ($C_{21}H_{22}ClF_3O_6NH_4^+$) 480.14, found 480.05. |
| 31 | Me | H | H | $OCF_3$ | F | H | ESI-MS [M + Na]$^+$ calc'd for ($C_{21}H_{22}F_4O_7Na^+$) 485.12, found 485.40. |
| 32 | $CF_3$ | F | H | F | H | F | ESI-MS [M + NH$_4$]$^+$ calc'd for ($C_{20}H_{18}F_6O_6NH_4^+$) 486.13, found 486.45. |
| 33 | Me | H | H | OMe | H | OMe | ESI-MS [M + NH$_4$]$^+$ calc'd for ($C_{22}H_{28}O_8NH_4^+$) 438.21, found 438.10. |
| 34 | Me | H | H | OMe | F | F | ESI-MS [M + NH$_4$]$^+$ calc'd for ($C_{21}H_{24}F_2O_7NH_4^+$) 444.18, found 444.20. |
| 35 | Me | H | H | F | OMe | F | ESI-MS [M + Na]$^+$ calc'd for ($C_{21}H_{24}F_2O_7Na^+$) 449.14, found 449.15. |
| 36 | Me | H | H | $OCF_3$ | H | F | ESI-MS [M + Na]$^+$ calc'd for ($C_{21}H_{22}F_4O_7Na^+$) 485.12, found 485.15. |
| 37 | Me | F | H | F | H | F | ESI-MS [M + Na]$^+$ calc'd for ($C_{20}H_{21}F_3O_6Na^+$) 437.12, found 437.00. |
| 38 | Me | H | H | F | cPr | H | ESI-MS [M + Na]$^+$ calc'd for ($C_{23}H_{27}FO_6Na^+$) 441.17, found 441.05. |
| 39 | Me | H | H | OMe | F | OMe | ESI-MS [M + NH$_4$]$^+$ calc'd for ($C_{22}H_{27}FO_8NH_4^+$) 456.20, found 456.25. |
| 40 | Me | H | F | H | Cl | Me | ESI-MS [M + Na]$^+$ calc'd for (C21H$_{24}$ClFO$_6$Na$^+$) 449.85, found 449.4. |
| 41 | Me | H | H | Cl | $CF_3$ | H | ESI-MS [M + Na]$^+$ calc'd for (C21H$_{22}$ClF$_3$O$_6$Na$^+$) 485.83, found 485.3. |
| 42 | Me | H | F | H | $CF_3$ | H | ESI-MS [M + Na]$^+$ calc'd for ($C_{21}H_{22}F_4O_6Na^+$) 469.38, found 469.4. |
| 43 | Me | H | F | H | H | $OCF_3$ | ESI-MS [M + Na]$^+$ calc'd for ($C_{21}H_{22}F_4O_7Na^+$) 485.38, found 485.4. |
| 44 | Me | H | F | H | H | Cl | ESI-MS [M + Na]$^+$ calc'd for ($C_{20}H_{22}ClFO_6Na^+$) 435.83, found 435.4. |
| 45 | Me | H | F | H | Me | F | ESI-MS [M + Na]$^+$ calc'd for ($C_{21}H_{24}F_2O_6Na^+$) 433.4, found 433.3. |
| 46 | Me | H | F | H | H | $CF_3$ | ESI-MS [M + Na]$^+$ calc'd for ($C_{21}H_{22}F_4O_6Na^+$) 469.38, found 469.4. |
| 47 | Me | H | F | H | Cl | F | ESI-MS [M + Na]$^+$ calc'd for ($C_{20}H_{21}ClF_2O_6Na^+$) 453.82, found 453.3. |
| 48 | Me | H | F | H | F | Cl | ESI-MS [M + Na]$^+$ calc'd for ($C_{20}H_{21}ClF_2O_6Na^+$) 453.82, found 453.3. |
| 49 | Me | H | F | F | $CF_3$ | H | ESI-MS [M + Na]$^+$ calc'd for ($C_{21}H_{21}F_5O_6Na^+$) 487.37, found 487.3. |
| 50 | Me | H | Cl | H | Me | F | ESI-MS [M + Na]$^+$ calc'd for ($C_{21}H_{24}ClFO_6Na^+$) 449.85, found 449.4. |
| 51 | Me | H | H | F | H | OcPr | ESI-MS [M + Na]$^+$ calc'd for ($C_{23}H_{27}FO_7Na^+$) 457.16, found 457.15. |
| 52 | Cl | F | H | F | H | F | ESI-MS [M + NH$_4$]$^+$ calc'd for ($C_{19}H_{18}ClF_3O_6NH_4^+$) 452.11, found 452.10. |
| 53 | Me | H | H | F | cPr | F | ESI-MS [M + NH$_4$]$^+$ calc'd for ($C_{23}H_{26}F_2O_6NH_4^+$) 454.20, found 454.20. |
| 54 | Me | H | F | H | H | cPr | ESI-MS [M + Na]$^+$ calc'd for ($C_{23}H_{27}FO_6Na_2^+$) 464.43, found 464.5. |
| 55 | Me | H | $OCF_3$ | H | H | Cl | ESI-MS [M + Na]$^+$ calc'd for ($C_{21}H_{22}ClF_3O_7Na^+$) 501.83, found 501.4. |
| 56 | Me | H | F | H | cPr | Cl | ESI-MS [M + NH$_4$]$^+$ calc'd for ($C_{23}H_{26}ClFO_6NH_4^+$) 470.17, found 470.15. |
| 57 | Me | H | H | F | Me | H | ESI-MS [M + NH$_4$]$^+$ calc'd for ($C_{21}H_{25}FO_6NH_4^+$) 410.20, found 410.20. |
| 58 | $CF_3$ | H | H | OMe | H | F | ESI-MS [M + NH$_4$]$^+$ calc'd for ($C_{21}H_{22}F_4O_7NH_4^+$) 480.16, found 480.15. |
| 59 | $CF_3$ | H | H | F | H | $CF_3$ | ESI-MS [M + NH$_4$]$^+$ calc'd for ($C_{21}H_{19}F_7O_6NH_4^+$) 518.14, found 518.10. |
| 60 | Me | H | H | F | H | Me | ESI-MS [M+NH$_4$]$^+$ calc'd for ($C_{21}H_{25}FO_6NH_4^+$) 410.20, found 410.20. |
| 61 | Me | H | H | OMe | H | $CF_3$ | ESI-MS [M + NH$_4$]$^+$ calc'd for ($C_{22}H_{25}F_3O_7NH_4^+$) 476.19, found 476.25. |
| 62 | Me | H | H | F | H | cPr | ESI-MS [M + NH$_4$]$^+$ calc'd for ($C_{23}H_{27}FO_6NH_4^+$) 436.21, found 436.25. |
| 63 | Me | H | H | OMe | $CH_3$ | F | ESI-MS [M + NH$_4$]$^+$ calc'd for ($C_{22}H_{27}FO_7NH_4^+$) 440.21, found 440.25. |
| 64 | Me | H | H | F | $CF_3$ | F | ESI-MS [M + Na]$^+$ calc'd for ($C_{21}H_{21}F_5O_6Na^+$) 487.12, found 487.10. |
| 65 | Me | H | H | OMe | H | Me | ESI-MS [M + NH$_4$]$^+$ calc'd for ($C_{22}H_{28}O_7NH_4^+$) 422.22, found 422.20. |

TABLE 1-continued

| Example number | R₁ | R₆ | R₂ | R₃ | R₄ | R₅ | MS characterization |
|---|---|---|---|---|---|---|---|
| 66 | Me | H | H | Me | $CF_3$ | H | ESI-MS $[M + NH_4]^+$ calc'd for $(C_{22}H_{25}F_3O_6NH_4^+)$ 460.19, found 460.15. |
| 67 | Me | H | H | $CF_3$ | $CF_3$ | H | ESI-MS $[M + Na]^+$ calc'd for $(C_{22}H_{22}F_6O_6Na^+)$ 519.12, found 519.10. |
| 68 | Me | H | H | $CF_3$ | H | Me | ESI-MS $[M + NH_4]^+$ calc'd for $(C_{22}H_{25}F_3O_6NH_4^+)$ 460.19, found 460.20. |
| 69 | Me | H | H | $CF_3$ | OMe | H | ESI-MS $[M + 2Na]^+$ calc'd for $(C_{22}H_{25}F_3O_7Na_2^+)$ 504.2, found 504.5. |
| 70 | Me | H | F | F | H | F | ESI-MS $[M + Na]^+$ calc'd for $(C_{20}H_{21}F_3O_6Na^+)$ 437.1, found 437.4. |
| 71 | Me | H | H | F | OMe | Cl | ESI-MS $[M + 2Na]^+$ calc'd for $(C_{21}H_{24}ClFO_7Na_2^+)$ 488.1, found 488.5. |
| 72 | Me | H | H | OiPr | H | F | ESI-MS $[M + 2Na]^+$ calc'd for $(C_{22}H_{29}FO_7Na_2^+)$ 482.2, found 482.6. |
| 73 | Me | H | H | F | F | Cl | ESI-MS $[M + Na]^+$ calc'd for $(C_{20}H_{21}ClF_2O_6Na^+)$ 453.1, found 453.3. |
| 74 | Me | H | H | $CF_3$ | H | $CF_3$ | ESI-MS $[M + Na]^+$ calc'd for $(C_{22}H_{22}F_6O_6Na^+)$ 519.13, found 519.4 |
| 75 | Me | H | H | $CF_3$ | H | H | ESI-MS $[M + Na]^+$ calc'd for $(C_{21}H_{23}F_3O_6Na^+)$ 451.15, found 451.3. |
| 76 | Me | H | H | OMe | $CF_3$ | H | ESI-MS $[M + Na]^+$ calc'd for $(C_{22}H_{25}F_3O_7Na^+)$ 481.2, found 481.4. |
| 77 | Me | H | H | F | H | H | ESI-MS $[M + 2Na]^+$ calc'd for $(C_{20}H_{23}FO_6Na_2^+)$ 424.15, found 424.4. |
| 78 | Me | H | H | OEt | H | F | ESI-MS $[M + Na]^+$ calc'd for $(C_{21}H_{23}F_3O_6Na^+)$ 451.15, found 451.3. |
| 79 | Me | H | H | $CF_2CF_3$ | H | H | ESI-MS $[M + Na]^+$ calc'd for $(C_{22}H_{25}F_3O_7Na^+)$ 481.2, found 481.4. |
| 80 | $CF_3$ | H | H | F | $CF_3$ | H | ESI-MS $[M + 2Na]^+$ calc'd for $(C_{20}H_{23}FO_6Na_2^+)$ 424.15, found 424.4. |
| 81 | Me | H | H | F | OEt | H | ESI-MS $[M + NH_4]^+$ calc'd for $(C_{22}H_{27}FO_7NH_4^+)$ 440.21, found 440.25. |
| 82 | Me | H | F | H | OMe | F | ESI-MS $[M + Na]^+$ calc'd for $(C_{21}H_{24}F_2O_7Na^+)$ 449.14, found 449.15. |
| 83 | Me | H | H | F | $CH_2NMe_2$ | H | ESI-MS $[M + 1]^+$ calc'd for $(C_{23}H_{30}FNO_6)$ 435.21, found 436.3. |
| 84 | Me | H | H | F | Me | Me | ESI-MS $[M + NH_4]^+$ calc'd for $(C_{22}H_{27}FO_6NH_4^+)$ 424.21, found 424.25. |
| 85 | Me | H | H | F | H | $CHF_2$ | ESI-MS $[M + NH_4]^+$ calc'd for $(C_{21}H_{23}F_3O_6NH_4^+)$ 446.18, found 446.15. |
| 86 | Me | H | H | $CHF_2$ | H | $CHF_2$ | ESI-MS $[M + NH_4]^+$ calc'd for $(C_{22}H_{24}F_4O_6NH_4^+)$ 478.18, found 478.15. |
| 87 | Me | H | H | OMe | $CF_3$ | F | ESI-MS $[M + NH_4]^+$ calc'd for $(C_{22}H_{24}F_4O_7NH_4^+)$ 494.18, found 494.25. |
| 88 | Me | H | H | F | F | Me | ESI-MS $[M + NH_4]^+$ calc'd for $(C_{21}H_{24}F_2O_6NH_4^+)$ 428.19, found 428.15. |
| 89 | Me | H | H | F | iPr | F | ESI-MS $[M + NH_4]^+$ calc'd for $(C_{23}H_{28}F_2O_6NH_4^+)$ 456.22, found 456.25. |
| 90 | Me | H | H | OiPr | H | $CF_3$ | ESI-MS $[M + NH_4]^+$ calc'd for $(C_{24}H_{29}F_3O_7NH_4^+)$ 504.22, found 504.25. |
| 91 | Me | H | H | F | OiPe | F | ESI-MS $[M + NH_4]^+$ calc'd for $(C_{24}H_{30}F_2O_7NH_4^+)$ 486.23, found 486.30. |
| 92 | Me | H | H | F | Pr | F | ESI-MS $[M + NH_4]^+$ calc'd for $(C_{23}H_{28}F_2O_6NH_4^+)$ 456.22, found 456.20. |
| 93 | Me | H | H | F | OiPr | F | ESI-MS $[M + NH_4]^+$ calc'd for $(C_{23}H_{28}F_2O_7NH_4^+)$ 472.21, found 472.30. |
| 94 | Me | H | H | F | Et | F | ESI-MS $[M + Na]^+$ calc'd for $(C_{22}H_{26}F_2O_6Na^+)$ 447.16, found 447.20. |
| 95 | Me | H | H | F | CHOHMe | F | ESI-MS $[M + NH_4]^+$ calc'd for $(C_{22}H_{26}F_2O_7NH_4^+)$ 458.20, found 458.15. |
| 96 | Me | H | H | F | OCHF2 | F | ESI-MS $[M + NH_4]^+$ calc'd for $(C_{21}H_{22}F_4O_7NH_4^+)$ 480.16, found 480.25. |
| 97 | $CF_3$ | H | H | F | F | F | ESI-MS $[M + Na]^+$ calc'd for $(C_{20}H_{18}F_6O_6Na^+)$ 491.09, found 490.95. |
| 98 | Me | H | H | H | F | H | ESI-MS $[M + NH_4]^+$ calc'd for $(C_{20}H_{23}FO_6NH_4^+)$ 396.18, found 396.25. |
| 99 | Me | H | H | H | Cl | H | ESI-MS $[M + NH_4]^+$ calc'd for $(C_{20}H_{23}ClO_6NH_4^+)$ 412.15, found 412.15. |
| 100 | Me | H | H | H | cPr | H | ESI-MS $[M + NH_4]^+$ calc'd for $(C_{23}H_{28}O_6NH_4^+)$ 418.22, found 418.20. |
| 101 | Me | H | H | F | $OCF_3$ | F | ESI-MS $[M + Na]^+$ calc'd for $(C_{21}H_{21}F_5O_7Na^+)$ 503.11, found 503.15. |
| 102 | Me | H | H | F | $CH_2OMe$ | F | ESI-MS $[M + NH_4]^+$ calc'd for $(C_{22}H_{26}F_2O_7NH_4^+)$ 458.20, found 458.25. |
| 103 | Me | H | H | F | CCH | F | ESI-MS $[M + NH_4]^+$ calc'd for $(C_{22}H_{22}F_2O_6NH_4^+)$ 438.17, found 438.20. |

TABLE 1-continued

| Example number | $R_1$ | $R_6$ | $R_2$ | $R_3$ | $R_4$ | $R_5$ | MS characterization |
|---|---|---|---|---|---|---|---|
| 104 | Me | H | H | F | NMe$_2$ | F | ESI-MS [M + H]$^+$ calc'd for (C$_{22}$H$_{27}$F$_2$NO$_6$H$^+$) 440.19, found 440.15. |
| 105 | Me | H | H | H | CF3 | H | ESI-MS [M + NH$_4$]$^+$ calc'd for (C$_{21}$H$_{23}$F$_3$O$_6$NH$_4^+$) 446.18, found 446.20. |
| 106 | Me | H | H | OMe | F | CF$_3$ | ESI-MS [M + NH$_4$]$^+$ calc'd for (C$_{22}$H$_{24}$F$_4$O$_7$NH$_4^+$) 494.18, found 494.15. |
| 107 | Me | H | H | F | CHOHMe | F | ESI-MS [M + NH$_4$]$^+$ calc'd for (C$_{22}$H$_{26}$F$_2$O$_7$NH$_4^+$) 458.20, found 458.15. |
| 108 | Me | H | H | F | CHOHMe | F | ESI-MS [M + NH$_4$]$^+$ calc'd for (C$_{22}$H$_{26}$F$_2$O$_7$NH$_4^+$) 458.20, found 458.15. |
| 109 | Me | H | H | F | H | N(CH$_3$)$_2$ | ESI-MS [M + H]+ calc'd for (C22H28FNO6H+) 422.20, found 422.25. |
| 110 | Me | H | H | CF$_3$ | F | F | ESI-MS [M + NH4]+ calc'd for (C21H21F5O6NH4+) 482.16, found 482.14. |

Biological Protocols Used to Evaluate the Compounds of Invention

The activities of the Examples 1-108 compounds above as FiMiH antagonists/inhibitors were obtained by the following assay(s), and results are provided in Table 2. Results not provided mean that the activities have not yet been tested.

Hemagglutination Inhibition Assay (HAI)

The hemagglutination inhibition (HAI) assay was performed with UTI89 bacteria and guinea pig red blood cells, as previously described (S. J. Hultgren, W. R. Schwan, A. J. Schaeffer, J. L. Duncan Infect. Immun. 1986, 54, 613-620 and Jarvis, C.; Han, Z.; Kalas, V.; Klein, R.; Pinkner, J. S.; Ford, B.; Binkley, J.; Cusumano, C. K.; Cusumano, Z.; Mydock-McGrane, L.; Hultgren, S. J.; Janetka, J. W., ChemMedChem 2016, 11, 367-373). Results are listed in Table 2. Values not listed were not tested.

General Assays for Obtaining AUC Oral h*μm, % F, and Ue % PO Values 1.1. Animals Male Wistar Han rats were purchased from Vital River Laboratory Animal Technology Co. Ltd (Beijing, China). The animals were approx. 6-8 weeks old with body weights of 200-300 g on the dosing date. The animals were housed in a 12-hour light/12-hour dark cycle environment and had free access to food and water. All animals were fed prior to dosing. Studies were approved by the Pharmaron Institutional Animal Care and Use Committee (IACUC).

1.2. Study Design

Male Wistar Han rats (n=3 per dose group) were assigned to 1 group as shown in the table below. Test article was administered as an intravenous infusion for 1 hour (1 mg/kg) at 5 mL/kg/h. After 48 h, animals received a single oral dose (5 mg/kg, free form) at a dose volume of 10 mL/kg, respectively. Blood samples were collected at various time points after IV infusion and PO administrations. Urine samples were collected at various time points after IV infusion and PO administrations.

| Group | Dose Level (mg/kg) | Infusion Rate (mL/kg/h) | Dose Volume (mL/kg) | Conc. (mg/mL) | Administration Route | No. of Animals |
|---|---|---|---|---|---|---|
| 1 | 1 | 5 | — | 0.2 | IV infusion | 3/Group |
| 2 | 5 | — | 10 | 0.5 | PO | 3/Group |

1.3. Formulation Preparation

Preparation of dosing for IV infusion administration (1 mg/kg):

Test article was dissolved in DMSO with vortexing and sonification to obtain a stock solution. An aliquot of the stock solution was mixed with 10% HP-β-CD in saline with vortexing to obtain a solution with concentration at 0.2 mg/mL of test article.

Preparation of dosing for PO administration (5 mg/kg):

Test article was added into 1% Methyl Cellulose with vortexing and sonication to obtain a homogeneous suspension with concentration at 0.5 mg/mL of test article.

1.4. Sample Collection

Blood Samples:

For IV infusion (1 mg/kg) administration, blood samples were collected from each animal at 0, 0.25, 0.5, 0.75, 1, 1.08, 1.25, 1.5, 1.75, 2, 3, 5, 8, 12, 24 hour post-dose.

For PO (5 mg/kg) administration, blood samples were collected from each animal at 0, 0.25, 0.5, 1, 1.5, 2, 3, 4, 6, 8, 12, 24 hour post-dose.

Blood samples (50 μL) were collected from each animal via jugular vein. These blood samples were placed into tubes containing K$_2$EDTA. Whole blood was mixed with same volume of water and inverted several times. The blood samples were stored at −75±15° C. until analysis.

Urine Samples:

For IV infusion (1 mg/kg) administration, urine samples were collected from each animal at 0-4, 4-8, 8-12, 12-24 hour post-dose.

For PO (5 mg/kg) administration, urine samples were collected from each animal at 0-4, 4-8, 8-12, 12-24 hour post-dose.

Urine samples were collected continuously into containers maintained over dry ice at the intervals outlined below and stored at −80° C. prior to analysis.

1.5. Preparation of Standard Solutions for LC-MS/MS Analysis 10 mg/mL of test article stock solution was diluted with DMSO to obtain a 1 mg/mL standard stock solution (free form).

Calibration standard working solutions were prepared at concentrations of 5, 10, 20, 50, 100, 500, 1000, 5000 and 10000 ng/mL by serial dilution of the standard stock solution in 50% acetonitrile in water. Quality control working solutions at concentrations of 10, 500 and 8000 ng/mL were prepared by serial dilution of the standard stock solution in 50% acetonitrile in water. These QC samples were prepared on the day of analysis in the same way as calibration standards.

1.6. Sample Treatment

5 μL of each calibration standard working solution (5, 10, 20, 50, 100, 500, 1000, 5000 and 10000 ng/mL) was added to 50 μL of blank Wistar Han rat blood (Blank blood: water=1:1) or urine to achieve calibration standards of 0.5-1000 ng/mL (0.5, 1, 2, 5, 10, 50, 100, 500, 1000 ng/mL) in a total volume of 55 μL. Quality Control (QC) samples at 1 ng/mL (low), 50 ng/mL (mid), 800 ng/mL (high) for blood or urine were prepared independently for those used for the calibration curves. These QC samples were prepared on the day of analysis in the same way as calibration standards.

55 μL of standards, 55 μL of QC samples or 55 μL of unknown samples (50 μL of blood or urine with 5 μL 50% acetonitrile) were mixed to 200 μL of acetonitrile containing IS (dexamethasone) to precipitate proteins. Then the samples were vortexed for 30 sec. After centrifugation at 4° C., 4700 rpm for 30 min, and 5 μL of the supernatant was injected into the LC-MS/MS system for quantitative analysis.

1.7. Pharmacokinetic Analysis

Test article blood and urine concentrations for each animal following IV infusion at 1 mg/kg and PO at 5 mg/kg were used to calculate pharmacokinetic parameters by employing a non-compartmental analysis (Phoenix TM WinNonlin® 7.0). The linear trapezoidal algorithm was used for AUC calculation.

AUC oral h*uM: Area under blood concentration-time profile (units: h*μM) following oral administration % F: Oral bioavailability (%) derived from the ratio of dose-normalised AUC following PO and IV administration Ue % PO: Percentage of oral dose eliminated unchanged in urine

TABLE 2

| Example number | HAI titer EC > 90 | AUC oral h*uM | % F | Ue % po |
|---|---|---|---|---|
| 1 | "++++" | "+" | "++" | "++" |
| 2 | "++++" | "+++" | "++" | "++" |
| 3 | "++++" | "+++" | "++" | "++" |
| 4 | "++++" | "+" | "++" | "++" |
| 5 | "++++" | "++" | "++" | "++" |
| 6 | "++++" | "+" | "++" | "++" |
| 7 | "++++" | "+++" | "+++" | "+++" |
| 8 | "++++" | "+" | "+++" | "++" |
| 9 | "++++" | "++" | "+++" | "+++" |
| 10 | "++++" | | | |
| 11 | "+++" | "++" | "+++" | "++" |
| 12 | "+++" | | | |
| 13 | "+++" | | | |
| 14 | "+++" | | | |
| 15 | "++++" | "+" | "++" | "++" |
| 16 | "++++" | "++" | "++" | "++" |
| 17 | "+++" | | | |
| 18 | "+++" | | | |
| 19 | "++++" | | | |
| 20 | "++++" | | | |
| 21 | "+++" | | | |
| 22 | "++++" | | | |
| 23 | "+++" | | | |
| 24 | "++++" | "+" | "++" | "++" |
| 25 | "++++" | | | |
| 26 | "++++" | | | |
| 27 | "+++" | | | |
| 28 | "+" | | | |
| 29 | "+++" | | | |
| 30 | "++++" | | | |
| 31 | "+++" | | | |
| 32 | "++++" | "+" | "++" | "++" |
| 33 | "++++" | | | |
| 34 | "++++" | | | |
| 35 | "++++" | | | |
| 36 | "++++" | | | |
| 37 | "++++" | | | |
| 38 | "+++" | | | |
| 39 | "++++" | | | |
| 40 | "+++" | | | |
| 41 | "++++" | | | |
| 42 | "+++" | | | |
| 43 | "+++" | | | |
| 44 | "+++" | | | |
| 45 | "++++" | | | |
| 46 | "+++" | | | |
| 47 | "++++" | | | |
| 48 | "+++" | | | |
| 49 | "+++" | | | |
| 50 | "+++" | | | |
| 51 | "++++" | | | |
| 52 | "+++" | | | |
| 53 | "++++" | | | |
| 54 | "+++" | | | |
| 55 | "+++" | | | |
| 56 | "+++" | | | |
| 57 | "+++" | | | |
| 58 | "++++" | | | |
| 59 | "++++" | | | |
| 60 | "+++" | | | |
| 61 | "++++" | "++" | "++" | "+" |
| 62 | "+++" | | | |
| 63 | "++++" | | | |
| 64 | "++++" | "++" | "++" | "++" |
| 65 | "+++" | | | |
| 66 | "++++" | | | |
| 67 | "++++" | | | |
| 68 | "++++" | | | |
| 69 | "++++" | | | |
| 70 | "++++" | | | |
| 71 | "++++" | | | |
| 72 | "++++" | | | |
| 73 | "++++" | "+" | "++" | "++" |
| 74 | "++++" | "++" | "++" | "+" |
| 75 | "+++" | | | |
| 76 | "++++" | | | |
| 77 | "+++" | | | |
| 78 | "++++" | | | |
| 79 | "+++" | | | |
| 80 | "++++" | | | |
| 81 | "++++" | | | |
| 82 | "++++" | | | |
| 83 | "++++" | | | |
| 84 | "++++" | | | |
| 85 | "++++" | | | |
| 86 | "++++" | | | |
| 87 | "++++" | | | |
| 88 | "++++" | | | |
| 89 | "++++" | | | |
| 90 | "+++" | | | |
| 91 | "++++" | | | |
| 92 | "++++" | | | |
| 93 | "++++" | "+" | "++" | "+" |
| 94 | "++++" | "+" | "++" | "+" |
| 95 | "++++" | | | |
| 96 | "++++" | | | |
| 97 | "++++" | | | |
| 98 | "+++" | | | |
| 99 | "+++" | | | |
| 100 | "+++" | | | |
| 101 | "++++" | "+" | "++" | "+" |
| 102 | "++++" | | | |
| 103 | "++++" | | | |
| 104 | "++++" | | | |
| 105 | "+++" | | | |

TABLE 2-continued

| | |
|---|---|
| 106 | "++++" |
| 107 | "++++" |
| 108 | "++++" |
| 109 | "++++" |
| 110 | "++++" |

Legend for Table 2

| AUC oral h*µM n = 3 | % F | Ue % po |
|---|---|---|
| "+" | <0.51 h · µM | <10% | <0.5% |
| "++" | 0.5 <= x <= 11 h · µM | 10 <= x <= 30% | 0.5 <= x <= 5% |
| "+++" | >1 h · µM | >30% | >5% |

HAI nM

| | |
|---|---|
| <50 | "++++" |
| 50-200 | "+++" |
| 201-1000 | "++" |
| >1000 | "+" |

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound which is

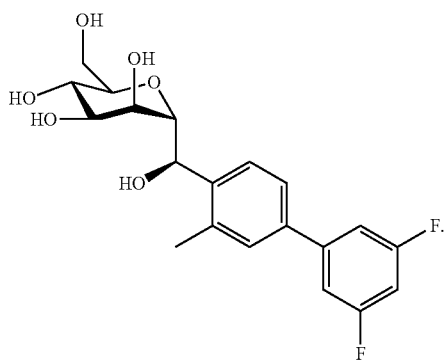

2. A pharmaceutical composition comprising the compound as recited in claim 1 together with a pharmaceutically acceptable carrier.

3. A pharmaceutical composition as recited in claim 2 formulated for oral administration.

4. The pharmaceutical composition as recited in claim 3, wherein said composition is chosen from a tablet and a capsule.

* * * * *

UNITED STATES PATENT AND TRADEMARK OFFICE
CERTIFICATE OF CORRECTION

Page 1 of 1

PATENT NO. : 11,111,262 B2
APPLICATION NO. : 17/063947
DATED : September 7, 2021
INVENTOR(S) : Michael Joseph Bishop et al.

It is certified that error appears in the above-identified patent and that said Letters Patent is hereby corrected as shown below:

In the Specification

Column 1, after Line 10, insert:
--STATEMENT REGARDING FEDERALLY SPONSORED RESEARCH OR DEVELOPMENT
This invention was made with government support under Award Number R44AI106112 awarded by the National Institute of Allergy and Infectious Diseases of the National Institutes of Health. The government has certain rights in the invention.--

Signed and Sealed this
Fifteenth Day of April, 2025

Coke Morgan Stewart
*Acting Director of the United States Patent and Trademark Office*